US007732607B2

(12) United States Patent
Mazurov et al.

(10) Patent No.: US 7,732,607 B2
(45) Date of Patent: Jun. 8, 2010

(54) HETEROARYL-SUBSTITUTED DIAZATRICYCLOALKANES AND METHODS OF USE THEREOF

(76) Inventors: Anatoly Mazurov, 3704 Timberoak Dr., Greensboro, NC (US) 27410; Lan Miao, 226 March Ferry Rd., Advance, NC (US) 27006; Jozef Klucik, 3389 Bridle Run Trail, Marietta, GA (US) 30064

( * ) Notice: Subject to any disclaimer, the term of this patent is extended or adjusted under 35 U.S.C. 154(b) by 916 days.

(21) Appl. No.: 11/465,914

(22) Filed: Aug. 21, 2006

(65) Prior Publication Data

US 2007/0197579 A1    Aug. 23, 2007

Related U.S. Application Data

(60) Provisional application No. 60/710,130, filed on Aug. 22, 2005.

(51) Int. Cl.
C07D 471/18     (2006.01)
A61K 31/439    (2006.01)
A61K 31/437    (2006.01)
(52) U.S. Cl. .................................. 546/84; 514/290
(58) Field of Classification Search .................. 546/84; 514/290
See application file for complete search history.

(56) References Cited

U.S. PATENT DOCUMENTS

| | | | |
|---|---|---|---|
| 4,922,901 A | 5/1990 | Brooks et al. |
| 5,187,166 A | 2/1993 | Kikuchi et al. |
| 5,583,140 A | 12/1996 | Bencherif et al. |
| 5,597,919 A | 1/1997 | Dull et al. |
| 5,604,231 A | 2/1997 | Smith et al. |
| 5,616,716 A | 4/1997 | Dull et al. |
| 5,663,356 A | 9/1997 | Ruecroft et al. |
| 5,672,601 A | 9/1997 | Cignarella |
| 5,712,270 A | 1/1998 | Sabb |
| 5,852,041 A | 12/1998 | Cosford et al. |
| 5,853,696 A | 12/1998 | Elmaleh |
| 5,952,339 A | 9/1999 | Bencherif et al. |
| 5,969,144 A | 10/1999 | London et al. |
| 6,310,043 B1 | 10/2001 | Bundle et al. |
| 7,101,890 B2 | 9/2006 | Czollner et al. |
| 7,115,629 B2 | 10/2006 | Gallemi et al. |
| 2001/0056084 A1 | 12/2001 | Allgeier et al. |
| 2002/0016371 A1 | 2/2002 | Shytle et al. |

FOREIGN PATENT DOCUMENTS

| | | |
|---|---|---|
| EP | 0 297858 A2 | 1/1989 |
| GB | 2 295 387 A | 5/1996 |
| WO | WO 94/08992 | 4/1994 |
| WO | WO 96/31475 | 10/1996 |
| WO | WO 96/40682 | 12/1996 |
| WO | WO 97/30998 | 8/1997 |
| WO | WO 98/25619 | 6/1998 |
| WO | WO 99/03859 | 1/1999 |
| WO | WO 99/21834 | 5/1999 |
| WO | WO 99/62505 | 12/1999 |
| WO | WO 00/73431 A2 | 12/2000 |
| WO | WO 01/36417 A1 | 5/2001 |
| WO | WO 02/15662 A2 | 2/2002 |
| WO | WO 02/16355 A2 | 2/2002 |
| WO | WO 02/16356 A2 | 2/2002 |
| WO | WO 02/16357 A2 | 2/2002 |
| WO | WO 02/16358 A2 | 2/2002 |
| WO | WO 02/17358 A2 | 2/2002 |
| WO | WO 02/051841 A1 | 7/2002 |
| WO | WO 2004/076449 A2 | 9/2004 |

OTHER PUBLICATIONS

Dorwald F. A. Side Reactions in Organic Synthesis, 2005, Wiley: VCH, Weinheim p. IX of Preface.*
Arneric, S., et al., "Preclinical Pharmacology of ABT-418: A Prototypical Cholinergic Channel Activator for the Potential Treatment of Alzheimer's Disease," *CNS Drug Rev.*, 1(1): 1-26 (1995).
Arneric, S., et al., "Cholinergic channel modulators as a novel therapeutic strategy for Alzheimer's disease," *Exp. Opin. Invest. Drugs*, 5(1): 79-100 (1996).
Arneric, S.P., and V.L., Villemagne, et al., (Eds.) *Neuronal Nicotinic Receptors: Pharmacology and Therapeutic Opportunities*, 235-250 (1998).
Bannon, A.W., et al., "Broad-Spectrum, Non-Opioid Analgesic Activity by Selective Modulation of Neuronal Nicotinic Acetylcholine Receptors," *Science*, 279: 77-81 (1998).

(Continued)

*Primary Examiner*—Rita J Desai
(74) *Attorney, Agent, or Firm*—Amy H. Fix; Womble Carlyle Sandridge & Rice PLLC

(57) ABSTRACT

The present invention relates to amide and urea derivatives of heteroaryl-substituted diazatricycloalkanes, pharmaceutical compositions including the compounds, methods of preparing the compounds, and methods of treatment using the compounds. More specifically, the methods of treatment involve modulating the activity of the α7 nAChR subtype by administering one or more of the compounds to treat or prevent disorders mediated by the α7 nAChR subtype. The diazatricycloalkanes typically consist of a 1-azabicyclooctane fused to pyrrolidine ring. The substitutent heteroaryl groups are 5- or 6-membered ring heteroaromatics, such as 3-pyridinyl and 5-pyrimidinyl moieties, which are attached directly to the diazatricycloalkane. The secondary nitrogen of the pyrrolidine moiety is substituted with an arylcarbonyl (amide type derivative) or an arylaminocarbonyl (N-arylcarbamoyl) (urea type derivative) group. The compounds are beneficial in therapeutic applications requiring a selective interaction at certain nAChR subtypes. That is, the compounds modulate the activity of certain nAChR subtypes, particularly the α7 nAChR subtype, and do not have appreciable activity toward muscarinic receptors. Radiolabeled versions of the compounds can be used in diagnostic methods.

8 Claims, No Drawings

OTHER PUBLICATIONS

Bencherif, M., and J. D. Schmitt, "Targeting Neuronal Nicotinic Receptors: a Path to New Therapies," *Current Drug Targets*, 1(4): 349-357 (2002).

Bencherif, M., and R.J. Lukas, "Ligand Binding and Functional Characterization of Muscarinic Acetylcholine Receptors on the TE671/RD Human Cell Line," *J. Pharmacol. Exp. Ther.*, 257(3): 946-953 (1991).

Bencherif, M., et al., "RJR-2403: A Nicotinic Agonist with CNS Selectivity I: In Vitro Characterization," *J. Pharmacol. Exper. Therapeutics*, 279(3): 1413-1421 (1996).

Bencherif M. and R.J. Lukas, "Differential Regulation of Nicotinic Acetylcholine Receptor Expression by Human TE671/RD Cells Following Second Messenger Modulation and Sodium Butyrate Treatments," *Mol Cell Neurosci.*, 2(1): 52-65 (1991).

Besidsky, Y., et al., "3'-Keto-1-nitro-2-phenylspiro[cyclopropane-3,2'-quinuclidine]: Synthesis and Reactions with Nucleophiles," *J. Heterocyclic Chem.*, 31: 1321-1326 (1994).

Besidsky, Y., et al., "Synthesis of Perhydro-1,4-ethano-1,5-naphthyridine and Perhydro-4,7-ethanopyrrolo[3,2-b]pyridine Derivatives: Potential $NK_1$-receptor Antagonists. X-Ray Molecular Structures of (4aR*,8S*,8aR*)-6-Oxo-8-phenylperhydro-1,4-ethano-1,5-naphthyridine and (4aR*,7R*,8R*,8aR*)-7,8-Diphenylperhydro-1,4-ethano-1,5-naphthyridine," *J.Chem. Soc., Perkin Trans.*, 465-480 (1995).

Brioni, J.D., et al., "The Pharmacology of (-)-Nicotine and Novel Cholinergic Channel Modulators," *Adv. Pharmacol.*, 37: 153-214 (1997).

Broadley, K.J., and D.R. Kelly, "Review Muscarinic Receptor Agonists and Antagonists," *Molecules*, 6: 142-193 (2001).

Caulfield, M.P., "Muscarinic Receptors-Characterization, Coupling, and Function," *Pharmac. Ther.*, 58: 319-379 (1993).

Cheng, Y-C., and W.H. Prusoff, "Relationship Between the Inhibition Constant ($K_1$) and the Concentration of Inhibitor which Causes 50 Per Cent inhibition ($I_{50}$) of an Enzymatic Reaction," *Biochem. Pharmacol.*, 22(23): 3099-3108 (1973).

Chiari, A., et al., "Sex Differences in Cholinergic Analgesia I: A Supplemental Nicotinic Mechanism in Normal Females," *Anesthesiology*, 91(5): 1447-1454 (1999).

Damaj, M.I., et al.,"Antinociceptive and Pharmacological Effects of Metanicotine, a Selective Nicotinic Agonist," *J. Pharmacol. Exp. Ther.*, 291(1): 390-398 (1999).

Decina, P., et al., "Cigarette Smoking and Neuroleptic-Induced Parkinsonism," *Biol. Psychiatry*, 28(6): 502-508 (1990).

Dolle, F., et al., "Synthesis and preliminary evaluation of a carbon-11-labelled agonist of the α-7 nicotinic acetylcholine receptor," *J. Labelled Comp. Radiopharm.*, 44: 785-795 (2001).

Fisher, A., et al., "The Fused Quinuclidine-Valerolactone System," *Tetrahedron*, 31(4): 317-325 (1975).

Freedman, R., et al., "Evidence in Postmortem Brain Tissue for Decreased Numbers of Hippocampal Nicotinic Receptors in Schizophrenia," *Biol. Psychiatry*, 38(1): 22-33 (1995).

Georgian, V., et al., "Bridged Quinuclidines: Synthesis of 5-Azatricyclo [$3.2.1.0^{2,7}$]octane. Incorporation of a Bridged Quinuclidine Into the Cinchona Aklaloid Skeleton," *Heterocycles*, 7(2): 1017-1025 (1977).

Gorbyleva, et al., Khim Geterotsikl. Soedin., *Chem. Abstracts*, 98: 34478a, 1232-1237 (1982).

Hall, G.H., and D.M. Turner, "Effects of Nicotine on the Release of $^3$H-Noradrenaline from the Hypothalamus," *Biochemical Pharmacology*, 21: 1829-1838 (1972).

Hamon, M., "Neuropharmacology of anxiety: perspectives and prospects," *TiPS*, 15: 36-39 (1994).

Harsing, Jr., et al., "Dopamine Efflux from Striatum After Chronic Nicotine: Evidence for Autoreceptor Desensitization," *J. Neurochem.*, 59(1): 48-54 (1992).

Heeschen, C., et al., "A novel angiogenic pathway mediated by non-neuronal nicotinic acetylcholine receptors," *J. Clin. Invest.*, 110(4): 527-536 (2002).

Hery, F., et al., "Control of the Release of Newly Synthetized $^3$H-5-Hydroxytryptamine by Nicotinic and Muscarinic Receptors in Rat Hypothalamic Slices," *Naunyn-Schmiedeberg's Arch. Pharmacol.*, 296: 91-97 (1977).

Holladay, M.W., et al., "Neuronal Nicotinic Acetylcholine Receptors as Targets for Drug Discovery," *J. Med. Chem.*, 40(26): 4169-4194 (1997).

Hoyer, D. and H.W.G.M. Boddeke, "Partial agonists, full agonists, antagonists: dilemmas of definition," *TiPS Reviews*, 14: 270-275 (1993).

Hughes, J., "S 40 Nicotine and Neuropsychiatric Disorders," Session 6, in *International Symposium on Nicotine: The Effects of Nicotine on Biological Systems II*, (Birkhäuser Verlag Publishers, 1994).

Jalilian, A.R., et al., "One-Step, No-Carrier-Added, Synthesis of a F-Labelled Benzodiazepine Receptor Ligand," *Journal of Labelled Compounds and Radiopharmaceuticals*, 43: 545-555 (2000).

Jeyarasasingam, G., et al., "Stimulation of Non-α7 Nicotinic Receptors Partially Protects Dopaminergic Neurons from 1-Methyl-4 Phenylpyridinium-Induced Toxicity in Culture," *Neuroscience*, 109(2): 275-285 (2002).

Lavand'homme, P., and J.C. Eisenach, "Sex Differences in Cholinergic Analgesia II: Differing Mechanisms in Two Models of Allodynia," *Anesthesiology*, 91(5): 1455-1461 (1999).

Leonard, S., et al., "Nicotinic Receptor Function in Schizophrenia," *Schizophrenia Bulletin*, 22(3): 431-445 (1996).

Levin, E.D., and A.H. Rezvani, "Nicotinic Treatment for Cognitive Dysfunction," *Current Drug Targets: CNS and Neurological Disorders*, 1(4): 423-431 (2002).

Lippiello, P.M., et al., "RJR-2403: A Nicotinic Agonist with CNS Selectivity II. In Vivo Characterization," *J. P. E. T.*, 279(3): 1422-1429 (1996).

Lowry, O.H., et al., "Protein Measurement with the Folin Phenol Reagent," *J. Biol. Chem.*, 193: 265-275 (1951).

Lukas, R.J., and M.J. Cullen, "An Isotopic Rubidium Ion Efflux Assay for the Functional Characterization of Nicotinic Acetylcholine Receptors on Clonal Cell Lines," *Anal. Biochem.*, 175(1): 212-218 (1988).

Lukas, R.J., "Pharmacological Distinctions between Functional Nicotinic Acetylcholine Receptors on the PC12 Rat Pheochromocytoma and the TE671 Human Medulloblastoma," *J. Pharmacol. Exp. Ther.*, 251(1): 175-182 (1989).

Lukas, R.J., et al., "Characterization of Nicotinic Acetylcholine Receptors Expressed by Cells of the SH-SY5Y Human Neuroblastoma Clonal Line," *Molec. Cellular Neurosci.*, 4(1): 1-12 (1993).

Luther, et al., "A Muscle Acetylcholine Receptor is Expressed in the Human Cerebellar Medulloblastoma Cell Line TE671," *J. Neurosci.* 9(3): 1082-1096 (1989).

Mach, R.H., et al., "F-Labeled Benzamides for Studying the Dopamine $D_2$ Receptor with Positron Emission Tomography," *J. Med. Chem.*, 36: 3707-3720 (1993).

Macor, J.E., et al., "The 5-$HT_3$ Antagonist Tropisetron (ICS 205-930) is a Potent and Selective α7 Nicotinic Receptor Partial Agonist," *Bioorg. Med. Chem. Lett.*, 11: 319-321 (2001).

Madhav, R., "Synthesis of 1,4-Ethano-3,4-dihydro-2H-1,5-naphthyridines," *Synthesis*, p. 27 (1982).

O'Neill, M.J., et al., "The Role of Neuronal Nicotinic Acetylcholine Receptors in Acute and Chronic Neurodegeneration," *Current Drug Targets: CNS and Neurological Disorders*, 1(4): 399-411 (2002).

Onaivi, E.S., et al., "Chronic Nicotine Reverses Age-Associated Increases in Tail-Flick Latency and Anxiety in Rats," *Life Sciences*, 54(3): 193-202 (1993).

Oswald, R.E., et al., "Characterization of nicotinic acetylcholine receptor channels of the TE671 human medulloblastoma clonal line," *Neurosci. Lett.*, 96: 207-212 (1989).

Pomerleau, O.F., et al., "The Effects of Cigarette Smoking on Pain and Anxiety," *Addictive Behaviors*, 9: 265-271 (1984).

Pullan, R.D., et al. "Transdermal Nicotine for Active Ulcerative Colitis," *New England J. Med.*, 330(12): 811-815 (1994).

Rapier, C., et al., "Stereoselective Nicotine-Induced Release of Dopamine from Striatal Synaptosomes: Concentration Dependence and Repetitive Stimulation," *J. Neurochem.*, 50(4): 1123-1130 (1988).

Rapier, C., et al., "Nicotinic Modulation of [³H]Dopamine Release from Striatal Synaptosomes: Pharmacological Characterisation," *J. Neurochem.*, 54(3): 937-45 (1990).

Romano, C., and A. Goldstein, "Stereospecific Nicotine Receptors on Rat Brain Membranes," *Science*, 210(7): 647-650 (1980).

Rowell, P.P., and D. Winkler, "Nicotinic Stimulation of [³ H] Acetylcholine Release from Mouse Cerebral Cortical Synaptosomes," *J. Neurochem.*, 43(6): 1593-1598 (1984).

Sanberg, P.R., et al., "Nicotine Potentiation of Haloperidol-Induced Catalepsy: Striatal Mechanisms," *Pharmacol. Biochem. & Behavior*, 46: 303-307 (1993).

Sandor, N.T., et al. "Effect of nicotine on dopaminergic-cholinergic interaction in the striatum," *Brain Res*,. 567: 313-316 (1991).

Schmitt, J., "Exploring the Nature of Molecular Recognition in Nicotinic Acetylcholine Receptors," *Curr. Med. Chem.*, 7(8): 749-800 (Aug. 2000).

Shestopalov, A.M., et al., "Cyclization of Nitriles," *J. Org. Chem. USSR* (*Engl. Trans.*) 25(9.2): 1789-1793 (1989).

Sjak-Shie, N.N. and E.M. Meyer, "Effects of chronic nicotine and pilocarpine administration on neocortocal neuronal density and [³H]GABA uptake in nucleus basalis lesioned rats," *Brain Res.*, 624: 295-298 (1993).

Stevens, K.E., et al., "Selective $\alpha_7$-nicotinic agonists normalize inhibition of auditory response in DBA mice," *Psychopharm.*, 136: 320-327 (1998).

Stratton, M.R., et al., "Characterization of the human cell line TE671," *Carcinogenesis*, 10(5): 899-905 (1989).

Toth, E., et al., "Effect of Nicotine of Extracellular Levels of Neurotransmitters Assessed by Microdialysis in Various Brain Regions: Role of Glutamic Acid," *Neurochem. Res.*, 17(3): 265-270 (1992).

Tracey, K. J., "The Inflammatory Reflex," *Nature*, 420: 853-859 (2002).

Tripathi, H.L., et al., "Nicotine-Induced Antinociception of Rats and Mice: Correlation with Nicotine Brain Levels," *J. Pharmacol. Exp. Ther.*, 221(1): 91-96 (1982).

Utsugisawa, K., et al., "Over-expression of $\alpha 7$ nicotinic acetylcholine receptor induces sustained ERK phosphorylation and N-cadherin expression in PC12 cells," *Molecular Brain Research* 106: 88-93 (2002).

Viti, G., et al., "Synthesis of a Benzo[b]-1,5-naphthyridine Derivative as a Potential Constrained $NK_1$ Receptor Antagonist," *Tetrahedron Letters*, 35(2): 5939-5942 (1994).

Vizi, E.S., "Acetylcholine release from guinea-pig ileum by parasympathetic ganglion stimulants and gastrin-like polypeptides," *Br. J. Pharmac.*, 47: 765-777 (1973).

Wagner, B., et al., "Does Smoking Reduce the Risk of Neuroleptic Parkinsonoids?," *Pharmacopsychiat.* 21: 302-303 (1988).

Wang, H., et al., "Nicotinic acetylcholine receptor $\alpha 7$ subunit is an essential regulator of inflammation," *Nature*, 421: 384-388 (2003).

Whiting, P.J., et al., "Expression of nicotinic acetylcholine receptor subtypes in brain and retina," *Brain Res Mol Brain Res.*, 10(1): 61-70 (1991).

Williams, M., et al., "Neuronal Nicotinic Acetylcholine Receptors," *Drug News Perspec.*, 7(4): 205-223 (1994).

Willstaetter and Kahn, *Chem. Ber.*, 37: 401-417 (1904).

Xiao, H-S, et al., "Identification of gene expression profile of dorsal root ganglion in the rat peripheral axotomy model of neuropathic pain," *Proc. Nat. Acad. Sci.*, 99(12): 8360-8365 (2002).

International Search Report (PCT/US2006/032685 / dated Jan. 10, 2007).

\* cited by examiner

HETEROARYL-SUBSTITUTED DIAZATRICYCLOALKANES AND METHODS OF USE THEREOF

This application claims benefit of U.S. Provisional Patent Application No. 60/710,130, filed Aug. 22, 2005, the contents of which are fully incorporated herein by reference.

FIELD OF THE INVENTION

The present invention relates to pharmaceutical compositions incorporating compounds capable of affecting nicotinic acetylcholinergic receptors (nAChRs), for example, as modulators of specific nicotinic receptor subtypes (specifically, the α7 nAChR subtype). The present invention also relates to methods for treating a wide variety of conditions and disorders, particularly those associated with dysfunction of the central and autonomic nervous systems.

BACKGROUND OF THE INVENTION

Nicotine has been proposed to have a number of pharmacological effects. See, for example, Pullan et al., *N. Engl. J. Med.* 330: 811 (1994). Certain of those effects may be related to effects upon neurotransmitter release. See, for example, Sjak-shie et al., *Brain Res.* 624: 295 (1993), where neuroprotective effects of nicotine are proposed. Release of acetylcholine and dopamine by neurons, upon administration of nicotine, has been reported by Rowell et al., *J. Neurochem.* 43: 1593 (1984); Rapier et al., *J. Neurochem.* 50: 1123 (1988); Sandor et al., *Brain Res.* 567: 313 (1991) and Vizi, Br. *J. Pharmacol.* 47: 765 (1973). Release of norepinephrine by neurons, upon administration of nicotine, has been reported by Hall et al., *Biochem. Pharmacol.* 21: 1829 (1972). Release of serotonin by neurons, upon administration of nicotine, has been reported by Hery et al., *Arch. Int. Pharmacodyn. Ther.* 296: 91 (1977). Release of glutamate by neurons, upon administration of nicotine, has been reported by Toth et al., *Neurochem Res.* 17: 265 (1992). Confirmatory reports and additional recent studies have included the modulation, in the central nervous system (CNS), of glutamate, nitric oxide, GABA, tachykinins, cytokines, and peptides (reviewed in Brioni et al., *Adv. Pharmacol.* 37: 153 (1997)). In addition, nicotine reportedly potentiates the pharmacological behavior of certain pharmaceutical compositions used for the treatment of certain disorders. See, for example, Sanberg et al., *Pharmacol. Biochem. & Behavior* 46: 303 (1993); Harsing et al., *J. Neurochem.* 59: 48 (1993) and Hughes, *Proceedings from Intl. Symp. Nic.* S40 (1994). Furthermore, various other beneficial pharmacological effects of nicotine have been proposed. See, for example, Decina et al., *Biol. Psychiatry* 28: 502 (1990); Wagner et al., *Pharmacopsychiatry* 21: 301 (1988); Pomerleau et al., *Addictive Behaviors* 9: 265 (1984); Onaivi et al., *Life Sci.* 54(3): 193 (1994); Tripathi et al., *JPET* 221: 91(1982) and Hamon, *Trends in Pharmacol. Res.* 15: 36 (1994).

Various compounds that target nAChRs have been reported as being useful for treating a wide variety of conditions and disorders. See, for example, Williams et al., *DN&P* 7(4): 205 (1994); Americ et al., *CNS Drug Rev.* 1(1): 1 (1995); Arneric et al., *Exp. Opin. Invest. Drugs* 5(1): 79 (1996); Bencherif et al., *JPET* 279: 1413 (1996); Lippiello et al., *JPET* 279: 1422 (1996); Damaj et al., *J. Pharmacol. Exp. Ther.* 291: 390 (1999); Chiari et al., *Anesthesiology* 91: 1447 (1999); Lavand'homme and Eisenbach, *Anesthesiology* 91: 1455 (1999); Holladay et al., *J. Med. Chem.* 40(28): 4169 (1997); Bannon et al., *Science* 279: 77 (1998); PCT WO 94/08992, PCT WO 96/31475, PCT WO 96/40682, and U.S. Pat. Nos. 5,583,140 to Bencherif et al., 5,597,919 to Dull et al., 5,604,231 to Smith et al., and 5,852,041 to Cosford et al. Nicotinic compounds are reported as being particularly useful for treating a wide variety of CNS disorders. Indeed, a wide variety of compounds have been reported to have therapeutic properties. See, for example, Bencherif and Schmitt, *Current Drug Targets: CNS and Neurological Disorders* 1(4): 349 (2002); Levin and Rezvani, *Current Drug Targets: CNS and Neurological Disorders* 1(4): 423 (2002); O'Neill et al., *Current Drug Targets: CNS and Neurological Disorders* 1(4): 399 (2002); U.S. Pat. Nos. 5,1871,166 to Kikuchi et al., 5,672,601 to Cignarella, PCT WO 99/21834, and PCT WO 97/40049, UK Patent Application GB 2295387, and European Patent Application 297,858.

CNS disorders are a type of neurological disorder. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin. Relatively common CNS disorders include presenile dementia (early-onset Alzheimer's disease), senile dementia (dementia of the Alzheimer's type), micro-infarct dementia, AIDS-related dementia, Creutzfeldt-Jakob disease, Pick's disease, Parkinsonism including Parkinson's disease, Lewy body dementia, progressive supranuclear palsy, Huntington's chorea, tardive dyskinesia, hyperkinesia, mania, attention deficit disorder, anxiety, dyslexia, schizophrenia, depression, obsessive-compulsive disorders and Tourette's syndrome.

The nAChRs characteristic of the CNS have been shown to occur in several subtypes, the most common of which are the α4β2 and α7 subtypes. See, for example, Schmitt, *Current Med. Chem.* 7: 749 (2000). Ligands that interact with the α7 nAChR subtype have been proposed to be useful in the treatment of schizophrenia. There are a decreased number of hippocampal nAChRs in postmortem brain tissue of schizophrenic patients. Also, there is improved psychological effect in smoking versus non-smoking schizophrenic patients. Nicotine improves sensory gating deficits in animals and schizophrenics. Blockade of the α7 nAChR subtype induces a gating deficit similar to that seen in schizophrenia. See, for example, Leonard et al., *Schizophrenia Bulletin* 22(3): 431 (1996). Biochemical, molecular, and genetic studies of sensory processing, in patients with the P50 auditory-evoked potential gating deficit, suggest that the α7 nAChR subtype may function in an inhibitory neuronal pathway. See, for example, Freedman et al., *Biological Psychiatry* 38(1): 22 (1995).

More recently, α7 nAChRs have been proposed to be mediators of angiogenesis, as described by Heeschen et al., *J. Clin. Invest.* 100: 527 (2002). In these studies, inhibition of the α7 subtype was shown to decrease inflammatory angiogenesis. Also, α7 nAChRs have been proposed as targets for controlling neurogenesis and tumor growth (Utsugisawa et al., *Molecular Brain Research* 106(1-2): 88 (2002) and U.S. Patent Application 2002/0016371). Finally, the role of the α7 subtype in cognition (Levin and Rezvani, *Current Drug Tar-* gets: CNS and Neurological Disorders* 1(4): 423 (2002)), neuroprotection (O'Neill et al., *Current Drug Targets: CNS and Neurological Disorders* 1(4): 399 (2002) and Jeyarasasingam et al., *Neuroscience* 109(2): 275 (2002)), and neuropathic pain (Xiao et al., *Proc. Nat. Acad. Sci.* (US) 99(12): 8360 (2002)) has recently been recognized.

Various compounds have been reported to interact with α7 nAChRs and have been proposed as therapies on that basis. See, for instance, PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998), Dolle et al., *J Labeled Comp. Radiopharm.* 44: 785 (2001) and Macor et al., *Bioorg. Med. Chem. Lett.* 11: 319 (2001) and references therein. Among these compounds, a common structural theme is that of the substituted tertiary bicyclic amine (e.g., quinuclidine). Similar substituted quinuclidine compounds have also been reported to bind at muscarinic receptors. See, for instance, U.S. Pat. No. 5,712,270 to Sabb and PCTs WO 02/00652 and WO 02/051841.

It would be desirable to provide a useful method for the prevention and treatment of a condition or disorder by administering a nicotinic compound to a patient susceptible to or suffering from such a condition or disorder. It would be highly beneficial to provide individuals suffering from certain disorders (e.g., CNS diseases) with interruption of the symptoms of those disorders by the administration of a pharmaceutical composition containing an active ingredient having nicotinic pharmacology which has a beneficial effect (e.g., upon the functioning of the CNS), but does not provide any significant associated side effects. It would be highly desirable to provide a pharmaceutical composition incorporating a compound that interacts with nAChRs, such as those that have the potential to affect the functioning of the CNS. It would be highly desirable that such a compound, when employed in an amount sufficient to affect the functioning of the CNS, would not significantly affect those nAChR subtypes that have the potential to induce undesirable side effects (e.g., appreciable activity at cardiovascular and skeletal muscle receptor sites). In addition, it would be highly desirable to provide a pharmaceutical composition incorporating a compound which interacts with nicotinic receptors but not muscarinic receptors, as the latter are associated with side effects, such as hypersalivation, sweating, tremors, cardiovascular and gastrointestinal disturbances, related to the function of the parasympathetic nervous system (see Caulfield, *Pharmacol. Ther.* 58: 319 (1993) and Broadley and Kelly, *Molecules* 6: 142 (2001)). Furthermore, it would be highly desirable to provide pharmaceutical compositions, which are selective for the α7 nAChR subtype, for the treatment of certain conditions or disorders (e.g., schizophrenia, cognitive disorders, and neuropathic pain) and for the prevention of tissue damage and the hastening of healing (i.e., for neuroprotection and the control of angiogenesis). The present invention provides such compounds, compositions and methods.

SUMMARY OF THE INVENTION

The present invention relates to amide and urea derivatives of heteroaryl-substituted diazatricycloalkanes, pharmaceutical compositions including the compounds, methods of preparing the compounds, and methods of treatment using the compounds. More specifically, the methods of treatment involve modulating the activity of the α7 nAChR subtype by administering one or more of the compounds to treat or prevent disorders mediated by the α7 nAChR subtype.

The diazatricycloalkanes typically consist of 1-azabicyclooctane fused to pyrrolidine ring. The substitutent heteroaryl groups are 5- or 6-membered ring heteroaromatics, such as 3-pyridinyl and 5-pyrimidinyl moieties, which are attached directly to the diazatricycloalkane. The secondary nitrogen of the pyrrolidine moiety is substituted with an arylcarbonyl (amide type derivative) or an arylaminocarbonyl (N-arylcarbamoyl) (urea type derivative) group.

The compounds are beneficial in therapeutic applications requiring a selective interaction at certain nAChR subtypes. That is, the compounds modulate the activity of certain nAChR subtypes, particularly the α7 nAChR subtype, and do not have appreciable activity toward muscarinic receptors. The compounds can be administered in amounts sufficient to affect the functioning of the central nervous system (CNS) without significantly affecting those receptor subtypes that have the potential to induce undesirable side effects (e.g., without appreciable activity at ganglionic and skeletal muscle nAChR sites and at muscarinic receptors). The compounds are therefore useful towards modulating release of ligands involved in neurotransmission, without appreciable side effects.

The compounds can be used as therapeutic agents to treat and/or prevent disorders characterized by an alteration in normal neurotransmitter release. Examples of such disorders include certain CNS conditions and disorders. The compounds can provide neuroprotection, treat patients susceptible to convulsions, treat depression, autism, and certain neuroendocrine disorders, and help manage stroke patients. The compounds also are useful in treating hypertension, type II diabetes and neoplasia and effecting weight loss. As the compounds are selective for the α7 nAChR subtype, they can be used to treat certain conditions or disorders (e.g., schizophrenia, cognitive disorders, and neuropathic pain), prevent tissue damage, and hasten healing (i.e., provide neuroprotection and control of angiogenesis).

The pharmaceutical compositions provide therapeutic benefit to individuals suffering from such conditions or disorders and exhibiting clinical manifestations of such conditions or disorders. The compounds, administered with the pharmaceutical compositions, can be employed in effective amounts to (i) exhibit nicotinic pharmacology and affect relevant nAChR sites (e.g., act as a pharmacological agonists at nicotinic receptors), and (ii) modulate neurotransmitter secretion, and hence prevent and suppress the symptoms associated with those diseases. In addition, the compounds have the potential to (i) increase the number of nAChRs of the brain of the patient, (ii) exhibit neuroprotective effects and (iii) when employed in effective amounts, not cause appreciable adverse side effects (e.g., significant increases in blood pressure and heart rate, significant negative effects upon the gastro-intestinal tract, and significant effects upon skeletal muscle). The pharmaceutical compositions are believed to be safe and effective with regards to prevention and treatment of various conditions or disorders.

The foregoing and other aspects of the present invention are explained in detail in the detailed description and examples set forth below.

DETAILED DESCRIPTION OF THE INVENTION

The compounds described herein have structures that are represented by Formula 1.

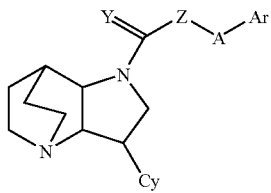

In Formula 1, Y is either oxygen or sulfur, and Z is either nitrogen (i.e., NR') or a covalent bond. A is either absent or a linker species selected from the group —CR'R"—, —CR'R"—CR'R"—, —CR'=CR'—, and —C$_2$—, wherein R' and R" are as hereinafter defined. Ar is an aryl group, either carbocyclic or heterocyclic, either monocyclic or fused polycyclic, unsubstituted or substituted; and Cy is a 5- or 6-membered heteroaromatic ring, unsubstituted or substituted. The junction between the azacycle and the azabicycle can be characterized by any of the various relative and absolute stereochemical configurations at the junction sites (e.g., cis or trans, R or S). The invention further includes pharmaceutically acceptable salts thereof. The compounds have one or more asymmetric carbons and can therefore exist in the form of racemic mixtures, enantiomers and diastereomers. In addition, some of the compounds exist as E and Z isomers about a carbon-carbon double bond. All these individual isomeric compounds and their mixtures are also intended to be within the scope of the present invention.

Thus, the invention includes compounds in which Ar is linked to the diazatricycle, at the nitrogen of the pyrrolidine ring, by a carbonyl group-containing functionality, forming an amide or a urea functionality. Ar may be bonded directly to the carbonyl group-containing functionality or may be linked to the carbonyl group-containing functionality through linker A. Furthermore, the invention includes compounds that contain a diazatricycle, containing a 1-azabicyclo[2.2.2]octane.

As used herein, "alkoxy" includes alkyl groups from 1 to 8 carbon atoms in a straight or branched chain, also C$_{3-8}$ cycloalkyl, bonded to an oxygen atom.

As used herein, "alkyl" includes straight chain and branched C$_{1-8}$ alkyl, preferably C$_{1-6}$ alkyl. "Substituted alkyl" defines alkyl substituents with 1-3 substituents as defined below in connection with Ar and Cy.

As used herein, "arylalkyl" refers to moieties, such as benzyl, wherein an aromatic is linked to an alkyl group that is linked to the indicated position in the compound of Formulas 1 or 2. "Substituted arylalkyl" defines arylalkyl substituents with 1-3 substituents as defined below in connection with Ar and Cy.

As used herein, "aromatic" refers to 3- to 10-membered, preferably 5- and 6-membered, aromatic and heteroaromatic rings and polycyclic aromatics including 5- and/or 6-membered aromatic and/or heteroaromatic rings.

As used herein, "aryl" includes both carbocyclic and heterocyclic aromatic rings, both monocyclic and fused polycyclic, where the aromatic rings can be 5- or 6-membered rings. Representative monocyclic aryl groups include, but are not limited to, phenyl, furanyl, pyrrolyl, thienyl, pyridinyl, pyrimidinyl, oxazolyl, isoxazolyl, pyrazolyl, imidazolyl, thiazolyl, isothiazolyl and the like. Fused polycyclic aryl groups are those aromatic groups that include a 5- or 6-membered aromatic or heteroaromatic ring as one or more rings in a fused ring system. Representative fused polycyclic aryl groups include naphthalene, anthracene, indolizine, indole, isoindole, benzofuran, benzothiophene, indazole, benzimidazole, benzthiazole, purine, quinoline, isoquinoline, cinnoline, phthalazine, quinazoline, quinoxaline, 1,8-naphthyridine, pteridine, carbazole, acridine, phenazine, phenothiazine, phenoxazine, and azulene.

As used herein, a "carbonyl group-containing functionality" is a moiety of the formula —C(=Y)—Z—, where Y are Z are as defined herein.

As used herein, "Cy" groups are 5- and 6-membered ring heteroaromatic groups. Representative Cy groups include pyridinyl, pyrimidinyl, furanyl, pyrrolyl, thienyl, oxazolyl, isoxazolyl, pyrazolyl, imidazolyl, thiazolyl, isothiazolyl and the like.

Individually, Ar and Cy, as well as the various positions on the 1,5-diazatricyclo[5.2.2.0<2,6>]undecane ring, can be unsubstituted or can be substituted with 1, 2 or 3 substitutents, such as alkyl, alkenyl, heterocyclyl, cycloalkyl, aryl, substituted aryl, arylalkyl, substituted arylalkyl, halo (e.g., F, Cl, Br, or I), —OR', —NR'R", —CF$_3$, —CN, —NO$_2$, —C$_2$R', —SR', —N$_3$, —C(=O)NR'R", —NR'C(=O)—R", —C(=O)R', —C(=O)OR', —OC(=O)R', —O(CR'R"),C (=O)R', —O(CR'R")$_r$NR"C(=O)R', —O(CR'R")$_r$ NR"SO$_2$R', —OC(=O)NR'R", —NR'C(=O)O—R", —SO$_2$R', —SO$_2$NR'R", and —NR'SO$_2$R", where R' and R" are individually hydrogen, lower alkyl (e.g., straight chain or branched alkyl including C$_1$-C$_8$, preferably C$_1$-C$_5$, such as methyl, ethyl, or isopropyl), cycloalkyl, heterocyclyl, aryl, or arylalkyl (such as benzyl), and r is an integer from 1 to 6. R' and R" can also combine to form a cyclic functionality.

As used herein, cycloalkyl radicals contain from 3 to 8 carbon atoms. Examples of suitable cycloalkyl radicals include, but are not limited to, cyclopropyl, cyclobutyl, cyclopentyl, cyclohexyl, cycloheptyl and cyclooctyl. As used herein, polycycloalkyl radicals are selected from adamantyl, bornanyl, norbornanyl, bornenyl and norbornenyl.

As used herein, halogen is chlorine, iodine, fluorine or bromine.

As used herein, heteroaryl radicals are rings that contain from 3 to 10 members, preferably 5 or 6 members, including one or more heteroatoms selected from oxygen, sulfur and nitrogen. Examples of suitable 5-membered ring heteroaryl moieties include furyl, pyrrolyl, imidazolyl, oxazolyl, thiazolyl, thienyl, tetrazolyl, and pyrazolyl. Examples of suitable 6-membered ring heteroaryl moieties include pyridinyl, pyrimidinyl, pyrazinyl, of which pyridinyl and pyrimidinyl are preferred.

As used herein, "heterocyclic" or "heterocyclyl" radicals include rings with 3 to 10 members, including one or more heteroatoms selected from oxygen, sulfur and nitrogen. Examples of suitable heterocyclic moieties include, but are not limited to, piperidinyl, morpholinyl, pyrrolidinyl, imidazolidinyl, pyrazolidinyl, isothiazolidinyl, thiazolidinyl, isoxazolidinyl, oxazolidinyl, piperazinyl, tetrahydropyranyl and tetrahydrofuranyl.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. Representative salts are provided as described in U.S. Pat. Nos. 5,597,919 to Dull et al., 5,616,716 to Dull et al. and 5,663,356 to Ruecroft et al.

As used herein, neurotransmitters whose release is modulated (i.e., increased or decreased, depending on whether the compounds function as agonists, partial agonists or antagonists) by the compounds described herein include, but are not limited to, acetylcholine, dopamine, norepinephrine, serotonin and glutamate, and the compounds described herein function as modulators of one or more nicotinic receptors.

As used herein, an "agonist" is a substance that stimulates its binding partner, typically a receptor. Stimulation is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Stimulation may be defined with respect to an increase in a particular effect or function that is induced by interaction of the agonist or partial agonist with a binding partner and can include allosteric effects.

As used herein, an "antagonist" is a substance that inhibits its binding partner, typically a receptor. Inhibition is defined in the context of the particular assay, or may be apparent in the literature from a discussion herein that makes a comparison to a factor or substance that is accepted as an "agonist" or an "antagonist" of the particular binding partner under substantially similar circumstances as appreciated by those of skill in the art. Inhibition may be defined with respect to a decrease in a particular effect or function that is induced by interaction of the antagonist with a binding partner, and can include allosteric effects.

As used herein, a "partial agonist" is a substance that provides a level of stimulation to its binding partner that is intermediate between that of a full or complete antagonist and an agonist defined by any accepted standard for agonist activity. It will be recognized that stimulation, and hence, inhibition is defined intrinsically for any substance or category of substances to be defined as agonists, antagonists, or partial agonists. As used herein, "intrinsic activity", or "efficacy," relates to some measure of biological effectiveness of the binding partner complex. With regard to receptor pharmacology, the context in which intrinsic activity or efficacy should be defined will depend on the context of the binding partner (e.g. receptor/ligand) complex and the consideration of an activity relevant to a particular biological outcome. For example, in some circumstances, intrinsic activity may vary depending on the particular second messenger system involved. See Hoyer and Boddeke, *Trends Pharmacol Sci.,* 14(7): 270 (1993). Where such contextually specific evaluations are relevant, and how they might be relevant in the context of the present invention, will be apparent to one of ordinary skill in the art.

In one embodiment, Cy is 3-pyridinyl or 5-pyrimidinyl, Y is oxygen, Z is a covalent bond and A is absent. In another embodiment, Cy is 3-pyridinyl or 5-pyrimidinyl, Y is oxygen, Z is nitrogen and A is absent. In a third embodiment, Cy is 3-pyridinyl or 5-pyrimidinyl, Y is oxygen, Z is a covalent bond, and A is a linker species. In a fourth embodiment, Cy is 3-pyridinyl or 5-pyrimidinyl, Y is oxygen, Z is nitrogen and A is a linker species.

Representative compounds of the present invention include:
5-benzoyl-3-pyridin-3-yl-1,5-diazatricyclo[5.2.2.0<2,6>]undecane,
5-(2-fluorobenzoyl)-3-pyridin-3-yl-1,5-diazatricyclo[5.2.2.0<2,6>]undecane,
5-(3-fluorobenzoyl)-3-pyridin-3-yl-1,5-diazatricyclo[5.2.2.0<2,6>]undecane,
5-(4-fluorobenzoyl)-3-pyridin-3-yl-1,5-diazatricyclo[5.2.2.0<2,6>]undecane,
5-(2-chlorobenzoyl)-3-pyridin-3-yl-1,5-diazatricyclo[5.2.2.0<2,6>]undecane,
5-(3-chlorobenzoyl)-3-pyridin-3-yl-1,5-diazatricyclo[5.2.2.0<2,6>]undecane,
5-(4-chlorobenzoyl)-3-pyridin-3-yl-1,5-diazatricyclo[5.2.2.0<2,6>]undecane,
5-(2-bromobenzoyl)-3-pyridin-3-yl-1,5-diazatricyclo[5.2.2.0<2,6>]undecane,
5-(3-bromobenzoyl)-3-pyridin-3-yl-1,5-diazatricyclo[5.2.2.0<2,6>]undecane,
5-(4-bromobenzoyl)-3-pyridin-3-yl-1,5-diazatricyclo[5.2.2.0<2,6>]undecane,
5-(2-iodobenzoyl)-3-pyridin-3-yl-1,5-diazatricyclo[5.2.2.0<2,6>]undecane,
5-(3-iodobenzoyl)-3-pyridin-3-yl-1,5-diazatricyclo[5.2.2.0<2,6>]undecane,
5-(4-iodobenzoyl)-3-pyridin-3-yl-1,5-diazatricyclo[5.2.2.0<2,6>]undecane,
5-(2-methylbenzoyl)-3-pyridin-3-yl-1,5-diazatricyclo[5.2.2.0<2,6>]undecane,
5-(3-methylbenzoyl)-3-pyridin-3-yl-1,5-diazatricyclo[5.2.2.0<2,6>]undecane,
5-(4-methylbenzoyl)-3-pyridin-3-yl-1,5-diazatricyclo[5.2.2.0<2,6>]undecane,
5-(2-methoxybenzoyl)-3-pyridin-3-yl-1,5-diazatricyclo[5.2.2.0<2,6>]undecane,
5-(3-methoxybenzoyl)-3-pyridin-3-yl-1,5-diazatricyclo[5.2.2.0<2,6>]undecane,
5-(4-methoxybenzoyl)-3-pyridin-3-yl-1,5-diazatricyclo[5.2.2.0<2,6>]undecane,
5-(2-methylthiobenzoyl)-3-pyridin-3-yl-1,5-diazatricyclo[5.2.2.0<2,6>]undecane,
5-(3-methylthiobenzoyl)-3-pyridin-3-yl-1,5-diazatricyclo[5.2.2.0<2,6>]undecane,
5-(4-methylthiobenzoyl)-3-pyridin-3-yl-1,5-diazatricyclo[5.2.2.0<2,6>]undecane,
5-(2-phenylbenzoyl)-3-pyridin-3-yl-1,5-diazatricyclo[5.2.2.0<2,6>]undecane,
5-(3-phenylbenzoyl)-3-pyridin-3-yl-1,5-diazatricyclo[5.2.2.0<2,6>]undecane,
5-(4-phenylbenzoyl)-3-pyridin-3-yl-1,5-diazatricyclo[5.2.2.0<2,6>]undecane,
5-(2-phenoxybenzoyl)-3-pyridin-3-yl-1,5-diazatricyclo[5.2.2.0<2,6>]undecane,
5-(3-phenoxybenzoyl)-3-pyridin-3-yl-1,5-diazatricyclo[5.2.2.0<2,6>]undecane,
5-(4-phenoxybenzoyl)-3-pyridin-3-yl-1,5-diazatricyclo[5.2.2.0<2,6>]undecane,
5-(2-phenylthiobenzoyl)-3-pyridin-3-yl-1,5-diazatricyclo[5.2.2.0<2,6>]undecane,
5-(3-phenylthiobenzoyl)-3-pyridin-3-yl-1,5-diazatricyclo[5.2.2.0<2,6>]undecane,
5-(4-phenylthiobenzoyl)-3-pyridin-3-yl-1,5-diazatricyclo[5.2.2.0<2,6>]undecane,
5-(2-cyanobenzoyl)-3-pyridin-3-yl-1,5-diazatricyclo[5.2.2.0<2,6>]undecane, 5-(3-cyanobenzoyl)-3-pyridin-3-yl-1,5-diazatricyclo[5.2.2.0<2,6>]undecane,
5-(4-cyanobenzoyl)-3-pyridin-3-yl-1,5-diazatricyclo[5.2.2.0<2,6>]undecane,
5-(2-trifluoromethylbenzoyl)-3-pyridin-3-yl-1,5-diazatricyclo[5.2.2.0<2,6>]undecane,
5-(3-trifluoromethylbenzoyl)-3-pyridin-3-yl-1,5-diazatricyclo[5.2.2.0<2,6>]undecane,
5-(4-trifluoromethylbenzoyl)-3-pyridin-3-yl-1,5-diazatricyclo[5.2.2.0<2,6>]undecane,
5-(2-dimethylaminobenzoyl)-3-pyridin-3-yl-1,5-diazatricyclo[5.2.2.0<2,6>]undecane,
5-(3-dimethylaminobenzoyl)-3-pyridin-3-yl-1,5-diazatricyclo[5.2.2.0<2,6>]undecane,
5-(4-dimethylaminobenzoyl)-3-pyridin-3-yl-1,5-diazatricyclo[5.2.2.0<2,6>]undecane,
5-(2-ethynylbenzoyl)-3-pyridin-3-yl-1,5-diazatricyclo[5.2.2.0<2,6>]undecane,
5-(3-ethynylbenzoyl)-3-pyridin-3-yl-1,5-diazatricyclo[5.2.2.0<2,6>]undecane,
5-(4-ethynylbenzoyl)-3-pyridin-3-yl-1,5-diazatricyclo[5.2.2.0<2,6>]undecane,
5-(3,4-dichlorobenzoyl)-3-pyridin-3-yl-1,5-diazatricyclo[5.2.2.0<2,6>]undecane,
5-(2,4-dimethoxybenzoyl)-3-pyridin-3-yl-1,5-diazatricyclo[5.2.2.0<2,6>]undecane,
5-(3,4,5-trimethoxybenzoyl)-3-pyridin-3-yl-1,5-diazatricyclo[5.2.2.0<2,6>]undecane,
5-(naphth-1-ylcarbonyl)-3-pyridin-3-yl-1,5-diazatricyclo[5.2.2.0<2,6>]undecane,
5-(naphth-2-ylcarbonyl)-3-pyridin-3-yl-1,5-diazatricyclo[5.2.2.0<2,6>]undecane,
5-(thien-2-ylcarbonyl)-3-pyridin-3-yl-1,5-diazatricyclo[5.2.2.0<2,6>]undecane,
5-(thien-3-ylcarbonyl)-3-pyridin-3-yl-1,5-diazatricyclo[5.2.2.0<2,6>]undecane,
5-(furan-2-ylcarbonyl)-3-pyridin-3-yl-1,5-diazatricyclo[5.2.2.0<2,6>]undecane,
5-(benzothien-2-ylcarbonyl)-3-pyridin-3-yl-1,5-diazatricyclo[5.2.2.0<2,6>]undecane,
5-(benzofuran-2-ylcarbonyl)-3-pyridin-3-yl-1,5-diazatricyclo[5.2.2.0<2,6>]undecane,
5-(7-methoxybenzofuran-2-ylcarbonyl)-3-pyridin-3-yl-1,5-diazatricyclo[5.2.2.0<2,6>]undecane, and
5-(1H-indol-3-ylcarbonyl)-3-pyridin-3-yl-1,5-diazatricyclo[5.2.2.0<2,6>]undecane.

Other compounds representative of the present invention include:
5-(phenylacetyl)-3-pyridin-3-yl-1,5-diazatricyclo[5.2.2.0<2,6>]undecane,
5-(diphenylacetyl)-3-pyridin-3-yl-1,5-diazatricyclo[5.2.2.0<2,6>]undecane,
5-(2-phenylpropanoyl)-3-pyridin-3-yl-1,5-diazatricyclo[5.2.2.0<2,6>]undecane, and
5-(3-phenylprop-2-enoyl)-3-pyridin-3-yl-1,5-diazatricyclo[5.2.2.0<2,6>]undecane.

Other compounds representative of the present invention include:
5-N-phenylcarbamoyl-3-pyridin-3-yl-1,5-diazatricyclo[5.2.2.0<2,6>]undecane,
5-(N-(2-fluorophenyl)carbamoyl)-3-pyridin-3-yl-1,5-diazatricyclo[5.2.2.0<2,6>]undecane,
5-(N-(3-fluorophenyl)carbamoyl)-3-pyridin-3-yl-1,5-diazatricyclo[5.2.2.0<2,6>]undecane,
5-(N-(4-fluorophenyl)carbamoyl)-3-pyridin-3-yl-1,5-diazatricyclo[5.2.2.0<2,6>]undecane,
5-(N-(2-chlorophenyl)carbamoyl)-3-pyridin-3-yl-1,5-diazatricyclo[5.2.2.0<2,6>]undecane,
5-(N-(3-chlorophenyl)carbamoyl)-3-pyridin-3-yl-1,5-diazatricyclo[5.2.2.0<2,6>]undecane,
5-(N-(4-chlorophenyl)carbamoyl)-3-pyridin-3-yl-1,5-diazatricyclo[5.2.2.0<2,6>]undecane,
5-(N-(2-bromophenyl)carbamoyl)-3-pyridin-3-yl-1,5-diazatricyclo[5.2.2.0<2,6>]undecane,
5-(N-(3-bromophenyl)carbamoyl)-3-pyridin-3-yl-1,5-diazatricyclo[5.2.2.0<2,6>]undecane,
5-(N-(4-bromophenyl)carbamoyl)-3-pyridin-3-yl-1,5-diazatricyclo[5.2.2.0<2,6>]undecane,
5-(N-(2-iodophenyl)carbamoyl)-3-pyridin-3-yl-1,5-diazatricyclo[5.2.2.0<2,6>]undecane,
5-(N-(3-iodophenyl)carbamoyl)-3-pyridin-3-yl-1,5-diazatricyclo[5.2.2.0<2,6>]undecane,
5-(N-(4-iodophenyl)carbamoyl)-3-pyridin-3-yl-1,5-diazatricyclo[5.2.2.0<2,6>]undecane,
5-(N-(2-methylphenyl)carbamoyl)-3-pyridin-3-yl-1,5-diazatricyclo[5.2.2.0<2,6>]undecane,
5-(N-(3-methylphenyl)carbamoyl)-3-pyridin-3-yl-1,5-diazatricyclo[5.2.2.0<2,6>]undecane,
5-(N-(4-methylphenyl)carbamoyl)-3-pyridin-3-yl-1,5-diazatricyclo[5.2.2.0<2,6>]undecane,
5-(N-(2-methoxyphenyl)carbamoyl)-3-pyridin-3-yl-1,5-diazatricyclo[5.2.2.0<2,6>]undecane,
5-(N-(3-methoxyphenyl)carbamoyl)-3-pyridin-3-yl-1,5-diazatricyclo[5.2.2.0<2,6>]undecane,
5-(N-(4-methoxyphenyl)carbamoyl)-3-pyridin-3-yl-1,5-diazatricyclo[5.2.2.0<2,6>]undecane,
5-(N-(2-methylthiophenyl)carbamoyl)-3-pyridin-3-yl-1,5-diazatricyclo[5.2.2.0<2,6>]undecane,
5-(N-(3-methylthiophenyl)carbamoyl)-3-pyridin-3-yl-1,5-diazatricyclo[5.2.2.0<2,6>]undecane,
5-(N-(4-methylthiophenyl)carbamoyl)-3-pyridin-3-yl-1,5-diazatricyclo[5.2.2.0<2,6>]undecane,
5-(N-(2-phenylphenyl)carbamoyl)-3-pyridin-3-yl-1,5-diazatricyclo[5.2.2.0<2,6>]undecane,
5-(N-(3-phenylphenyl)carbamoyl)-3-pyridin-3-yl-1,5-diazatricyclo[5.2.2.0<2,6>]undecane,
5-(N-(4-phenylphenyl)carbamoyl)-3-pyridin-3-yl-1,5-diazatricyclo[5.2.2.0<2,6>]undecane,
5-(N-(2-phenoxyphenyl)carbamoyl)-3-pyridin-3-yl-1,5-diazatricyclo[5.2.2.0<2,6>]undecane,
5-(N-(3-phenoxyphenyl)carbamoyl)-3-pyridin-3-yl-1,5-diazatricyclo[5.2.2.0<2,6>]undecane,
5-(N-(4-phenoxyphenyl)carbamoyl)-3-pyridin-3-yl-1,5-diazatricyclo[5.2.2.0<2,6>]undecane,
5-(N-(2-phenylthiophenyl)carbamoyl)-3-pyridin-3-yl-1,5-diazatricyclo[5.2.2.0<2,6>]undecane,
5-(N-(3-phenylthiophenyl)carbamoyl)-3-pyridin-3-yl-1,5-diazatricyclo[5.2.2.0<2,6>]undecane,
5-(N-(4-phenylthiophenyl)carbamoyl)-3-pyridin-3-yl-1,5-diazatricyclo[5.2.2.0<2,6>]undecane,
5-(N-(2-cyanophenyl)carbamoyl)-3-pyridin-3-yl-1,5-diazatricyclo[5.2.2.0<2,6>]undecane,
5-(N-(3-cyanophenyl)carbamoyl)-3-pyridin-3-yl-1,5-diazatricyclo[5.2.2.0<2,6>]undecane,
5-(N-(4-cyanophenyl)carbamoyl)-3-pyridin-3-yl-1,5-diazatricyclo[5.2.2.0<2,6>]undecane,
5-(N-(2-trifluoromethylphenyl)carbamoyl)-3-pyridin-3-yl-1,5-diazatricyclo[5.2.2.0<2,6>]undecane,
5-(N-(3-trifluoromethylphenyl)carbamoyl)-3-pyridin-3-yl-1,5-diazatricyclo[5.2.2.0<2,6>]undecane,
5-(N-(4-trifluoromethylphenyl)carbamoyl)-3-pyridin-3-yl-1,5-diazatricyclo[5.2.2.0<2,6>]undecane, 5-(N-(2-dimethylaminophenyl)carbamoyl)-3-pyridin-3-yl-1,5-diazatricyclo[5.2.2.0<2,6>]undecane,
5-(N-(3-dimethylaminophenyl)carbamoyl)-3-pyridin-3-yl-1,5-diazatricyclo[5.2.2.0<2,6>]undecane,
5-(N-(4-dimethylaminophenyl)carbamoyl)-3-pyridin-3-yl-1,5-diazatricyclo[5.2.2.0<2,6>]undecane,
5-(N-(2-ethynylphenyl)carbamoyl)-3-pyridin-3-yl-1,5-diazatricyclo[5.2.2.0<2,6>]undecane,
5-(N-(3-ethynylphenyl)carbamoyl)-3-pyridin-3-yl-1,5-diazatricyclo[5.2.2.0<2,6>]undecane,
5-(N-(4-ethynylphenyl)carbamoyl)-3-pyridin-3-yl-1,5-diazatricyclo[5.2.2.0<2,6>]undecane,
5-(N-(3,4-dichlorophenyl)carbamoyl)-3-pyridin-3-yl-1,5-diazatricyclo[5.2.2.0<2,6>]undecane,
5-(N-(2,4-dimethoxyphenyl)carbamoyl)-3-pyridin-3-yl-1,5-diazatricyclo[5.2.2.0<2,6>]undecane,
5-(N-(3,4,5-trimethoxyphenyl)carbamoyl)-3-pyridin-3-yl-1,5-diazatricyclo[5.2.2.0<2,6>]undecane,
5-(N-(1-naphthyl)carbamoyl)-3-pyridin-3-yl-1,5-diazatricyclo[5.2.2.0<2,6>]undecane, and
5-(N-(2-naphthyl)carbamoyl)-3-pyridin-3-yl-1,5-diazatricyclo[5.2.2.0<2,6>]undecane.

Other compounds representative of the present invention include:
5-(N-benzylcarbamoyl)-3-pyridin-3-yl-1,5-diazatricyclo[5.2.2.0<2,6>]undecane,
5-(N-(4-bromobenzyl)carbamoyl)-3-pyridin-3-yl-1,5-diazatricyclo[5.2.2.0<2,6>]undecane,
5-(N-(4-methoxybenzyl)carbamoyl)-3-pyridin-3-yl-1,5-diazatricyclo[5.2.2.0<2,6>]undecane,
5-(N-(1-phenylethyl)carbamoyl)-3-pyridin-3-yl-1,5-diazatricyclo[5.2.2.0<2,6>]undecane, and
5-(N-(diphenylmethyl)carbamoyl)-3-pyridin-3-yl-1,5-diazatricyclo[5.2.2.0<2,6>]undecane.

In each of these compounds, a 3-pyridin-3-yl-1,5-diazatricyclo[5.2.2.0<2,6>]undecane moiety has the structure, with a partial numbering scheme provided, shown below:

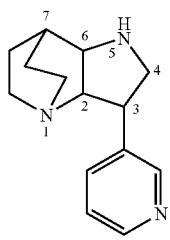

The nitrogen at the position indicated above as the 5-position is the nitrogen involved in the formation of the amides, thioamides, ureas and thioureas described herein.

In each of these compounds, individual isomers thereof, mixtures thereof, including racemic mixtures, enantiomers, diastereomers and tautomers thereof, and the pharmaceutically acceptable salts thereof, are intended to be within the scope of the present invention.

I. METHODS OF PREPARING THE COMPOUNDS

The manner in which compounds of the present invention can be prepared can vary. While other synthetic strategies will be apparent to those of skill in the art, the compounds of Formula 1 can be made by cyclization of aldol condensation products formed from heteroaromatic aldehydes and 1-azabicyclo[2.2.2]octan-3-one. Thus, when 3-quinuclidinone hydrochloride is reacted with pyridine-3-carboxaldehyde (available from Aldrich Chemical Company), in the presence of methanolic potassium hydroxide, 2-((3-pyridinyl)methylene)-1-azabicyclo[2.2.2]octan-3-one results. A variety of heteroaromatic aldehydes can be used in the aldol condensation, in place of pyridine-3-carboxaldehyde (variation at Cy). Treatment of 2-((3-pyridinyl)methylene)-1-azabicyclo[2.2.2]octan-3-one with nitromethane and sodium methoxide results in conjugate addition of the nitromethane anion to the enone functionality. The nitro group, of 2-(1-(3-pyridinyl)-2-nitroethyl)-1-azabicyclo[2.2.2]octan-3-one thus produced, is then reduced with Raney nickel to give the corresponding amine. Under the reaction conditions (Raney nickel in ethanol), intramolecular reductive amination then takes place, producing 3-pyridin-3-yl-1,5-diazatricyclo[5.2.2.0<2,6>]undecane. This scaffold contains a secondary nitrogen, in the pyrrolidine ring, will react with a variety of acylating agents (e.g., acid chlorides, acid anhydrides, active esters, and carboxylic acids in the presence of coupling reagents), to form amide derivatives, and isocyanates, to produce urea derivatives (variation at Z-A-AR). The amide and urea derivatives are thus easily prepared using methods known to those skilled in the art of organic synthesis. Commercially unavailable isocyanates can be prepared in situ from corresponding amines and triphosgene in the presence of triethylamine. This chemistry can be accomplished in 96-well plate format to make libraries of such derivatives.

In some cases, reactive groups on Cy or AR may require protection. Methods described by Greene and Wuts, *Protective Groups in Organic Synthesis* 2$^{nd}$ ed., Wiley-Interscience Pub. (1991) can be used to protect and deprotect these reactive groups.

The compounds can be isolated and purified using methods well known to those of skill in the art, including, for example, crystallization, chromatography and/or extraction.

The compounds of general Formula 1 can be obtained in optically pure form by separating their racemates in accordance with the customary methods.

The compounds of general Formula 1 can optionally be converted into addition salts with a mineral or organic acid by the action of such an acid in an appropriate solvent, for example, an organic solvent such as an alcohol, a ketone, an ether or a chlorinated solvent. These salts likewise form part of the invention.

Representative pharmaceutically acceptable salts include, but are not limited to, benzenesulphonate, hydrobromide, hydrochloride, citrate, ethanesulphonate, fumarate, gluconate, iodate, maleate, isethionate, methanesulphonate, methylenebis(β-oxynaphthoate), nitrate, oxalate, palmoate, phosphate, salicylate, succinate, sulphate, tartrate, theophyllinacetate, p-toluenesulphonate, hemigalactarate and galactarate salts.

Imaging Agents

Certain compounds of the present invention can be synthesized in such a manner as to incorporate a radionuclide useful in diagnostic imaging. Of particular interest are those compounds that include radioactive isotopic moieties such as $^{11}C$, $^{18}F$, $^{76}Br$, $^{123}I$, $^{125}I$, and the like. The compounds can be radiolabeled at any of a variety of positions. For example, a radionuclide of the halogen series may be used within an alkyl halide or aryl halide moiety or functionality, while a radionuclide such as $^{11}C$ may be used with an alkyl (e.g., methyl) moiety or functionality.

For instance, commercially available p-(dimethylamino) benzoic acid (Aldrich) is converted, by treatment with iodomethane in methanol, into p-(trimethylammonium)benzoate, as described by Willstaetter and Kahn, *Chem. Ber.* 37:

406 (1904). The displacement of the trimethylammonium group by fluoride has been reported, in similar compounds, by several researchers (see, for instance, Mach et al., *J. Med. Chem.* 36: 3707 (1993) and Jalalian et al., *J. Labeled Compd. Radiopharm.* 43: 545 (2000)). These nucleophilic aromatic substitution reactions are typically carried out in dimethylsulfoxide (with or without water cosolvent), using KF or CsF as the source of fluoride ion (when KF is used, often Kryptofix® 222 is added). When $^{18}F^-$ is used in such a displacement, p-$^{18}$fluorobenzoic acid results. This carboxylic acid can be rapidly coupled to the NH group at the 5-position of a compound of the formula:

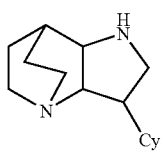

where Cy is as described above, and wherein the Cy and 1,5-diazatricyclo[5.2.2.0<2,6>]undecane ring can be functionalized with the various substituents described above, to form the desired p-$^{18}$fluorobenzamide derivative, using any of a variety of techniques known to those skilled in the art (some of which are described previously). The resulting compound can be used to specifically image α7 nAChRs. The related urea compound can be prepared by replacing the p-$^{18}$fluorobenzoic acid with a compound that includes a $^{18}$fluoroalkyl or $^{18}$fluoroarylalkyl N—C(O)—O-alkyl or other activated group with the NH group at the 5-position of the starting material described above. Similarly, the related thiourea or thioamide compounds can be prepared by replacing the p-$^{18}$fluorobenzoic acid with ap-$^{18}$fluorothiobenzoic acid, thiobenzoic acid or with a compound that includes an N—C(S)—O-alkyl or other activated group with the NH group at the 5-position of the starting material described above.

This same starting material can be readily radiolabeled by reacting the amine group at the 5-position with an activating agent such as ethyl chloroformate to form an N—C(O)-ethoxy group (or other activated carbonyl compound), which in turn is reacted with a radiolabeled aryl or arylalkyl amine (i.e., to form aryl ureas or arylalkyl ureas, where the radiolabel is on the aryl or arylalkyl moiety). An example of a radiolabeled aryl amine is aniline-UL-$^{14}$C, which is commercially available from SigmaAldrich. Alternatively, a radiolabeled aryl or arylalkyl isocyanate can be reacted with the amine at the 5-position to form a radiolabeled urea group. For example, bromophenyl-p-isocyanate (carbonyl $^{14}$C) is commercially available from American Radiolabeled Chemicals, Inc.

The resulting radiolabeled compounds can be purified by semi-preparative or preparative HPLC and briefly isolated for reconstitution.

The required amine-containing precursor compounds are described in detail above, and the resulting radiolabeled compounds can be used to specifically image α7 nAChRs.

II. PHARMACEUTICAL COMPOSITIONS

The compounds described herein can be incorporated into pharmaceutical compositions and used to prevent a condition or disorder in a subject susceptible to such a condition or disorder, and/or to treat a subject suffering from the condition or disorder. The pharmaceutical compositions described herein include one or more compounds of Formula 1 and/or pharmaceutically acceptable salts thereof. Chiral compounds can be employed as racemic mixtures or as pure enantiomers.

The manner in which the compounds are administered can vary. The compositions are preferably administered orally (e.g., in liquid form within a solvent such as an aqueous or non-aqueous liquid, or within a solid carrier). Preferred compositions for oral administration include pills, tablets, capsules, caplets, syrups, and solutions, including hard gelatin capsules and time-release capsules. Compositions can be formulated in unit dose form, or in multiple or subunit doses. Preferred compositions are in liquid or semisolid form. Compositions including a liquid pharmaceutically inert carrier such as water or other pharmaceutically compatible liquids or semisolids can be used. The use of such liquids and semisolids is well known to those of skill in the art.

The compositions can also be administered via injection, i.e., intravenously, intramuscularly, subcutaneously, intraperitoneally, intraarterially, intrathecally; and intracerebroventricularly. Intravenous administration is the preferred method of injection. Suitable carriers for injection are well known to those of skill in the art and include 5% dextrose solutions, saline, and phosphate-buffered saline. The compounds can also be administered as an infusion or injection (e.g., as a suspension or as an emulsion in a pharmaceutically acceptable liquid or mixture of liquids).

The formulations can also be administered using other means, for example, rectal administration. Formulations useful for rectal administration, such as suppositories, are well known to those of skill in the art. The compounds can also be administered by inhalation (e.g., in the form of an aerosol either nasally or using delivery articles of the type set forth in U.S. Pat. No. 4,922,901 to Brooks et al., the disclosure of which is incorporated herein in its entirety); topically (e.g., in lotion form); or transdermally (e.g., using a transdermal patch, using technology that is commercially available from Novartis and Alza Corporation). Although it is possible to administer the compounds in the form of a bulk active chemical, it is preferred to present each compound in the form of a pharmaceutical composition or formulation for efficient and effective administration.

Exemplary methods for administering such compounds will be apparent to the skilled artisan. The usefulness of these formulations can depend on the particular composition used and the particular subject receiving the treatment. These formulations can contain a liquid carrier that can be oily, aqueous, emulsified or contain certain solvents suitable to the mode of administration.

The compositions can be administered intermittently or at a gradual, continuous, constant or controlled rate to a warm-blooded animal (e.g., a mammal such as a mouse, rat, cat, rabbit, dog, pig, cow, or monkey), but advantageously are administered to a human being. In addition, the time of day and the number of times per day that the pharmaceutical formulation is administered can vary.

Preferably, upon administration, the active ingredients interact with receptor sites within the body of the subject that affect the functioning of the CNS. More specifically, in treating a CNS disorder, preferable administration is designed to optimize the effect upon those relevant nicotinic acetylcholine receptor (nAChR) subtypes that have an effect upon the functioning of the CNS, while minimizing the effects upon muscle-type receptor subtypes. Other suitable methods for administering the compounds of the present invention are described in U.S. Pat. No. 5,604,231 to Smith et al., the contents of which are hereby incorporated by reference.

In certain circumstances, the compounds described herein can be employed as part of a pharmaceutical composition with other compounds intended to prevent or treat a particular disorder. In addition to effective amounts of the compounds described herein, the pharmaceutical compositions can also include various other components as additives or adjuncts. Exemplary pharmaceutically acceptable components or adjuncts which are employed in relevant circumstances include antioxidants, free-radical scavenging agents, peptides, growth factors, antibiotics, bacteriostatic agents, immunosuppressives, anticoagulants, buffering agents, anti-inflammatory agents, anti-pyretics, time-release binders, anesthetics, steroids, vitamins, minerals and corticosteroids. Such components can provide additional therapeutic benefit, act to affect the therapeutic action of the pharmaceutical composition, or act towards preventing any potential side effects that can be imposed as a result of administration of the pharmaceutical composition.

The appropriate dose of the compound is that amount effective to prevent occurrence of the symptoms of the disorder or to treat some symptoms of the disorder from which the patient suffers. By "effective amount", "therapeutic amount" or "effective dose" is meant that amount sufficient to elicit the desired pharmacological or therapeutic effects, thus resulting in effective prevention or treatment of the disorder.

When treating a CNS disorder, an effective amount of compound is an amount sufficient to pass across the blood-brain barrier of the subject, to bind to relevant receptor sites in the brain of the subject and to modulate the activity of relevant nAChR subtypes (e.g., provide neurotransmitter secretion, thus resulting in effective prevention or treatment of the disorder). Prevention of the disorder is manifested by delaying the onset of the symptoms of the disorder. Treatment of the disorder is manifested by a decrease in the symptoms associated with the disorder or an amelioration of the recurrence of the symptoms of the disorder. Preferably, the effective amount is sufficient to obtain the desired result, but insufficient to cause appreciable side effects.

The effective dose can vary, depending upon factors such as the condition of the patient, the severity of the symptoms of the disorder, and the manner in which the pharmaceutical composition is administered. For human patients, the effective dose of typical compounds generally requires administering the compound in an amount sufficient to modulate the activity of relevant nAChRs to effect neurotransmitter (e.g., dopamine) release, but the amount should be insufficient to induce effects on skeletal muscles and ganglia to any significant degree. The effective dose of compounds will of course differ from patient to patient, but in general includes amounts starting where CNS effects or other desired therapeutic effects occur but below the amount where muscular effects are observed.

The compounds, when employed in effective amounts in accordance with the method described herein, are selective to certain relevant nAChRs, but do not significantly activate receptors associated with undesirable side effects at concentrations at least greater than those required for eliciting the release of dopamine or other neurotransmitters. By this is meant that a particular dose of compound effective in preventing and/or treating a CNS disorder is essentially ineffective in eliciting activation of certain ganglionic-type nAChRs at concentration higher than 5 times, preferably higher than 100 times, and more preferably higher than 1,000 times than those required for modulation of neurotransmitter release. This selectivity of certain compounds described herein against those ganglionic-type receptors responsible for cardiovascular side effects is demonstrated by a lack of the ability of those compounds to activate nicotinic function of adrenal chromaffin tissue at concentrations greater than those required for activation of dopamine release.

The compounds described herein, when employed in effective amounts in accordance with the methods described herein, can provide some degree of prevention of the progression of CNS disorders, ameliorate symptoms of CNS disorders, and ameliorate to some degree of the recurrence of CNS disorders. The effective amounts of those compounds are typically below the threshold concentration required to elicit any appreciable side effects, for example those effects relating to skeletal muscle. The compounds can be administered in a therapeutic window in which certain CNS disorders are treated and certain side effects are avoided. Ideally, the effective dose of the compounds described herein is sufficient to provide the desired effects upon the CNS but is insufficient (i.e., is not at a high enough level) to provide undesirable side effects. Preferably, the compounds are administered at a dosage effective for treating the CNS disorders but less than $\frac{1}{5}$, and often less than $\frac{1}{10}$, the amount required to elicit certain side effects to any significant degree.

Most preferably, effective doses are at very low concentrations, where maximal effects are observed to occur, with a minimum of side effects. Typically, the effective dose of such compounds generally requires administering the compound in an amount of less than 5 mg/kg of patient weight. Often, the compounds of the present invention are administered in an amount from less than about 1 mg/kg patent weight and usually less than about 100 µg/kg of patient weight, but frequently between about 10 µg to less than 100 µg/kg of patient weight. For compounds that do not induce effects on muscle-type nicotinic receptors at low concentrations, the effective dose is less than 5 mg/kg of patient weight; and often such compounds are administered in an amount from 50 µg to less than 5 mg/kg of patient weight. The foregoing effective doses typically represent that amount administered as a single dose, or as one or more doses administered over a 24-hour period.

For human patients, the effective dose of typical compounds generally requires administering the compound in an amount of at least about 1, often at least about 10, and frequently at least about 100 mg/24 hr/patient. For human patients, the effective dose of typical compounds requires administering the compound which generally does not exceed about 500, often does not exceed about 400, and frequently does not exceed about 300 mg/24 hr/patient. In addition, the compositions are advantageously administered at an effective dose such that the concentration of the compound within the plasma of the patient normally does not exceed 50 ng/mL, often does not exceed 30 ng/mL, and frequently does not exceed 10 ng/mL.

III. METHODS OF USING THE COMPOUNDS AND/OR PHARMACEUTICAL COMPOSITIONS

The compounds can be used to treat those types of conditions and disorders for which other types of nicotinic compounds have been proposed as therapeutics. See, for example, Williams et al., *Drug News Perspec.* 7(4): 205 (1994); Arneric et al., *CNS Drug Rev.* 1(1): 1 (1995); Arneric et al., *Exp. Opin. Invest. Drugs* 5(1): 79 (1996); Bencherif et al., *J. Pharmacol. Exp. Ther.* 279: 1413 (1996); Lippiello et al., *J. Pharmacol. Exp. Ther.* 279: 1422 (1996); Damaj et al., *J. Pharmacol. Exp. Ther.* 291: 390 (1999); Chiari et al., *Anesthesiology* 91: 1447 (1999); Lavand'homme and Eisenbach, *Anesthesiology* 91: 1455 (1999); Holladay et al., *J. Med. Chem.* 40(28): 4169 (1997); Bannon et al., *Science* 279: 77 (1998), PCT WO 94/08992, PCT WO 96/31475, and U.S. Pat. Nos. 5,583,140 to Bencherif et al., 5,597,919 to Dull et al., and 5,604,231 to Smith et al., the disclosures of each of which are incorporated herein by reference in their entirety.

More particularly, the compounds can be used to treat those types of conditions and disorders for which nicotinic compounds with selectivity for the α7 nAChR subtype have been proposed as therapeutics. See, for example, Leonard et al., *Schizophrenia Bulletin* 22(3): 431 (1996); Freedman et al., *Biological Psychiatry* 38(1): 22 (1995); Heeschen et al., *J. Clin. Invest.* 100: 527 (2002); Utsugisawa et al., *Molecular Brain Research* 106(1-2): 88 (2002); U.S. Patent Application 2002/0016371, Levin and Rezvani, *Current Drug Targets: CNS and Neurological Disorders* 1(4): 423 (2002); O'Neill et al., *Current Drug Targets. CNS and Neurological Disorders* 1(4): 399 (2002); Jeyarasasingam et al., *Neuroscience* 109(2): 275 (2002); Xiao et al., *Proc. Nat. Acad. Sci.* (US) 99(12): 8360 (2002); PCT WO 99/62505, PCT WO 99/03859, PCT WO 97/30998, PCT WO 01/36417, PCT WO 02/15662, PCT WO 02/16355, PCT WO 02/16356, PCT WO 02/16357, PCT WO 02/16358, PCT WO 02/17358, Stevens et al., *Psychopharm.* 136: 320 (1998); Dolle et al., *J. Labeled Comp. Radiopharm.* 44: 785 (2001) and Macor et al., *Bioorg. Med. Chem. Lett.* 11: 319 (2001) and references therein, the contents of each of which are hereby incorporated by reference in their entirety.

The compounds can also be used as adjunct therapy in combination with existing therapies in the management of the aforementioned types of diseases and disorders. In such situations, it is preferably to administer the active ingredients in a manner that minimizes effects upon nAChR subtypes such as those that are associated with muscle and ganglia. This can be accomplished by targeted drug delivery and/or by adjusting the dosage such that a desired effect is obtained without meeting the threshold dosage required to achieve significant side effects. The pharmaceutical compositions can be used to ameliorate any of the symptoms associated with those conditions, diseases and disorders. Representative classes of disorders that can be treated are discussed in detail below.

Treatment of CNS Disorders

Examples of conditions and disorders that can be treated include neurological disorders and neurodegenerative disorders, and, in particular, CNS disorders. CNS disorders can be drug induced; can be attributed to genetic predisposition, infection or trauma; or can be of unknown etiology. CNS disorders comprise neuropsychiatric disorders, neurological diseases and mental illnesses, and include neurodegenerative diseases, behavioral disorders, cognitive disorders and cognitive affective disorders. There are several CNS disorders whose clinical manifestations have been attributed to CNS dysfunction (i.e., disorders resulting from inappropriate levels of neurotransmitter release, inappropriate properties of neurotransmitter receptors, and/or inappropriate interaction between neurotransmitters and neurotransmitter receptors). Several CNS disorders can be attributed to a deficiency of choline, dopamine, norepinephrine and/or serotonin.

Examples of CNS disorders that can be treated in accordance with the present invention include pre-senile dementia (early onset Alzheimer's disease), senile dementia (dementia of the Alzheimer's type), Lewy Body dementia, micro-infarct dementia, AIDS-related dementia, HIV-dementia, multiple cerebral infarcts, Parkinsonism including Parkinson's disease, Pick's disease, progressive supranuclear palsy, Huntington's chorea, tardive dyskinesia, hyperkinesia, mania, attention deficit disorder, anxiety, depression, dyslexia, schizophrenia, obsessive-compulsive disorders, Tourette's syndrome, mild cognitive impairment (MCI), age-associated memory impairment (AAMI), premature amnesic and cognitive disorders which are age-related or a consequence of alcoholism, or immunodeficiency syndrome, or are associated with vascular disorders, with genetic alterations (such as, for example, trisomy 21) or with attention deficiencies or learning deficiencies, acute or chronic neurodegenerative conditions such as amyotrophic lateral sclerosis, multiple sclerosis, peripheral neurotrophies, and cerebral or spinal traumas. In addition, the compounds can be used to treat nicotine addiction and/or other behavioral disorders related to substances that lead to dependency (e.g., alcohol, cocaine, heroin and opiates, psychostimulants, benzodiazepines and barbiturates).

Schizophrenia is an example of a CNS disorder that is particularly amenable to treatment by modulating the α7 nAChR subtype. The compounds can also be administered to improve cognition and/or provide neuroprotection, and these uses are also particularly amenable to treatment with compounds, such as the compounds of the present invention, that are specific for the α7 nAChR subtype.

The disorders can be treated and/or prevented by administering to a patient in need of treatment or prevention thereof an effective treatment or preventative amount of a compound that provides some degree of prevention of the progression of a CNS disorder (i.e., provides protective effects), ameliorating the symptoms of the disorder, and ameliorating the recurrence of the disorder.

Anti-Inflammatory Uses

Excessive inflammation and tumor necrosis factor (TNF) synthesis cause morbidity and even mortality in a variety of diseases. These diseases include, but are not limited to, endotoxemia, sepsis, rheumatoid arthritis, and irritable bowel disease. The nervous system, primarily through the vagus nerve, is known to regulate the magnitude of the innate immune response by inhibiting the release of macrophage tumor necrosis factor. This physiological mechanism is known as the "cholinergic anti-inflammatory pathway" (see, for example, Tracey, *Nature.* 420(6917): 853 (2002)).

The nAChR α7 subunit is required for acetylcholine inhibition of macrophage TNF release, and also inhibits release of other cytokines. Agonists (or, at elevated dosages, partial agonists) at the α7-specific nAChR subtype can inhibit the TNF-modulated inflammatory response. Accordingly, those compounds described herein that are α7 agonists can be used to treat inflammatory disorders characterized by excessive synthesis of TNF (see also Wang et al., *Nature*, 421(6921): 384 (2003)).

Inflammatory conditions that can be treated or prevented by administering the compounds described herein include, but are not limited to chronic and acute inflammation, psoriasis, gout, acute pseudogout, acute gouty arthritis, arthritis, rheumatoid arthritis, osteoarthritis, allograft rejection, chronic transplant rejection, asthma, atherosclerosis, mononuclear-phagocyte dependent lung injury, idiopathic pulmonary fibrosis, atopic dermatitis, chronic obstructive pulmonary disease, adult respiratory distress syndrome, acute chest syndrome in sickle cell disease, inflammatory bowel disease, Crohn's disease, ulcerative colitis, acute cholangitis, aphteous stomatitis, glomerulonephritis, lupus nephritis, thrombosis, and graft vs. host reaction.

Minimizing the Inflammatory Response Associated with Bacterial and/or Viral Infection Many bacterial and/or viral infections are associated with side effects brought on by the formation of toxins, and the body's natural response to the bacteria or virus and/or the toxins. Examples of such bacterial infections include anthrax, botulism, and sepsis. As discussed above, the body's response to infection often involves generating a significant amount of tumor necrosis factor and/or other cytokines. The over-expression of these cytokines can result in significant injury, such as septic shock (when the bacteria is sepsis), endotoxic shock, urosepsis and toxic shock syndrome.

Cytokine expression is mediated by the α7 nAChR and can be inhibited by administering agonists or partial agonists of these receptors. Those compounds described herein that are agonists or partial agonists of these receptors can therefore be used to minimize the inflammatory response associated with bacterial infection, as well as viral and fungal infections. Certain of the compounds themselves may also have antimicrobial properties.

These compounds can also be used as adjunct therapy in combination with existing therapies to manage bacterial, viral and fungal infections, such as antibiotics, antivirals and antifungals. Antitoxins can also be used to bind to toxins produced by the infectious agents and allow the bound toxins to pass through the body without generating an inflammatory response. Examples of antitoxins are disclosed, for example, in U.S. Pat. No. 6,310,043 to Bundle et al., incorporated herein by reference. Other agents effective against bacterial and other toxins can be effective and their therapeutic effect can be complimented by co-administration with the compounds described herein.

Analgesic Uses

The compounds can be administered to treat and/or prevent pain, including neurologic, neuropathic and chronic pain. The analgesic activity of compounds described herein can be demonstrated in models of persistent inflammatory pain and of neuropathic pain, performed as described in U.S. Published Patent Application No. 20010056084 A1 to Allgeier et al. (e.g., mechanical hyperalgesia in the complete Freund's adjuvant rat model of inflammatory pain and mechanical hyperalgesia in the mouse partial sciatic nerve ligation model of neuropathic pain).

The analgesic effect is suitable for treating pain of various genesis or etiologies, in particular in treating inflammatory pain and associated hyperalgesia, neuropathic pain and associated hyperalgesia, chronic pain (e.g., severe chronic pain, post-operative pain and pain associated with various conditions including cancer, angina, renal or biliary colic, menstruation, migraine and gout) and fibromyalgia syndrome. Inflammatory pain may be of diverse genesis, including arthritis and rheumatoid disease, teno-synovitis and vasculitis. Neuropathic pain includes trigeminal or herpetic neuralgia, diabetic neuropathy pain, causalgia, low back pain and deafferentation syndromes such as brachial plexus avulsion.

Inhibition of Neovascularization

The α7 nAChR is also associated with neovascularization. Inhibition of neovascularization, for example, by administering antagonists (or at certain dosages, partial agonists) of the α7 nAChR can inhibit neovascularization and, accordingly, treat or prevent conditions characterized by undesirable neovascularization or angiogenesis. Such conditions can include those characterized by inflammatory angiogenesis and/or ischemia-induced angiogenesis. Neovascularization associated with tumor growth can also be inhibited by administering those compounds described herein that function as antagonists or partial agonists of α7 nAChR.

Specific antagonism of α7 nAChR-specific activity reduces the angiogenic response to inflammation, ischemia, and neoplasia. Guidance regarding appropriate animal model systems for evaluating the compounds described herein can be found, for example, in Heeschen, et al., J. Clin Invest, 110(4): 527 (2002), incorporated herein by reference regarding disclosure of α7-specific inhibition of angiogenesis and cellular (in vitro) and animal modeling of angiogenic activity relevant to human disease, especially the Lewis lung tumor model (in vivo, in mice—see, in particular, pages 529, and 532-533).

Representative tumor types that can be treated using the compounds described herein include NSCLC, ovarian cancer, pancreatic cancer, breast carcinoma, colon carcinoma, rectum carcinoma, lung carcinoma, oropharynx carcinoma, hypopharynx carcinoma, esophagus carcinoma, stomach carcinoma, pancreas carcinoma, liver carcinoma, gallbladder carcinoma, bile duct carcinoma, small intestine carcinoma, urinary tract carcinoma, kidney carcinoma, bladder carcinoma, urothelium carcinoma, female genital tract carcinoma, cervix carcinoma, uterus carcinoma, ovarian carcinoma, choriocarcinoma, gestational trophoblastic disease, male genital tract carcinoma, prostate carcinoma, seminal vesicles carcinoma, testes carcinoma, germ cell tumors, endocrine gland carcinoma, thyroid carcinoma, adrenal carcinoma, pituitary gland carcinoma, skin carcinoma, hemangiomas, melanomas, sarcomas, bone and soft tissue sarcoma, Kaposi's sarcoma, tumors of the brain, tumors of the nerves, tumors of the eyes, tumors of the meninges, astrocytomas, gliomas, glioblastomas, retinoblastomas, neuromas, neuroblastomas, Schwannomas, meningiomas, solid tumors arising from hematopoietic malignancies (such as leukemias, chloromas, plasmacytomas and the plaques and tumors of mycosis fungoides and cutaneous T-cell lymphoma/leukemia), and solid tumors arising from lymphomas.

The compounds can also be administered in conjunction with other forms of anti-cancer treatment, including co-administration with antineoplastic antitumor agents such as cisplatin, adriamycin, daunomycin, and the like, and/or anti-VEGF (vascular endothelial growth factor) agents, as such are known in the art.

The compounds can be administered in such a manner that they are targeted to the tumor site. For example, the compounds can be administered in microspheres, microparticles or liposomes conjugated to various antibodies that direct the microparticles to the tumor. Additionally, the compounds can be present in microspheres, microparticles or liposomes that are appropriately sized to pass through the arteries and veins, but lodge in capillary beds surrounding tumors and administer the compounds locally to the tumor. Such drug delivery devices are known in the art.

Other Disorders

In addition to treating CNS disorders, inflammatory disorders, and neovascular disorders, and inhibiting the pain response, the compounds can be also used to prevent or treat certain other conditions, diseases, and disorders. Examples include autoimmune disorders such as Lupus, disorders associated with cytokine release, cachexia secondary to infection (e.g., as occurs in AIDS, AIDS related complex and neoplasia), as well as those indications set forth in PCT WO 98/25619. The compounds can also be administered to treat convulsions such as those that are symptomatic of epilepsy, and to treat conditions such as syphilis and Creutzfeldt-Jakob disease.

Diagnostic Uses

The compounds can be used in diagnostic compositions, such as probes, particularly when they are modified to include appropriate labels. The probes can be used, for example, to determine the relative number and/or function of specific receptors, particularly the α7 receptor subtype. The compounds of the present invention most preferably are labeled with a radioactive isotopic moiety such as $^{11}C$, $^{18}F$, $^{76}Br$, $^{123}I$ or $^{125}I$, as discussed above.

The administered compounds can be detected using known detection methods appropriate for the label used. Examples of detection methods include position emission topography (PET) and single-photon emission computed tomography (SPECT). The radiolabels described above are useful in PET (e.g., $^{11}$C, $^{18}$F or $^{76}$Br) and SPECT (e.g., $^{123}$I) imaging, with half-lives of about 20.4 minutes for $^{11}$C, about 109 minutes for $^{18}$F, about 13 hours for $^{123}$I, and about 16 hours for $^{76}$Br. A high specific activity is desired to visualize the selected receptor subtypes at non-saturating concentrations. The administered doses typically are below the toxic range and provide high contrast images. The compounds are expected to be capable of administration in non-toxic levels. Determination of dose is carried out in a manner known to one skilled in the art of radiolabel imaging. See, for example, U.S. Pat. No. 5,969,144 to London et al.

The compounds can be administered using known techniques. See, for example, U.S. Pat. No. 5,969,144 to London et al. The compounds can be administered in formulation compositions that incorporate other ingredients, such as those types of ingredients that are useful in formulating a diagnostic composition. Compounds useful in accordance with carrying out the present invention most preferably are employed in forms of high purity. See, for example, U.S. Pat. No. 5,853,696 to Elmalch et al.

After the compounds are administered to a subject (e.g., a human subject), the presence of that compound within the subject can be imaged and quantified by appropriate techniques in order to indicate the presence, quantity, and functionality of selected nicotinic cholinergic receptor subtypes. In addition to humans, the compounds can also be administered to animals, such as mice, rats, dogs, and monkeys. SPECT and PET imaging can be carried out using any appropriate technique and apparatus. See Villemagne et al., In: Americ et al., (Eds.) *Neuronal Nicotinic Receptors Pharmacology and Therapeutic Opportunities*, 235-250 (1998) and U.S. Pat. No. 5,853,696 to Elmalch et al. for a disclosure of representative imaging techniques.

The radiolabeled compounds bind with high affinity to selective nAChR subtypes (e.g., α7) and preferably exhibit negligible non-specific binding to other nicotinic cholinergic receptor subtypes (e.g., those receptor subtypes associated with muscle and ganglia). As such, the compounds can be used as agents for noninvasive imaging of nAChR subtypes within the body of a subject, particularly within the brain for diagnosis associated with a variety of CNS diseases and disorders.

In one aspect, the diagnostic compositions can be used in a method to diagnose disease in a subject, such as a human patient. The method involves administering to that patient a detectably labeled compound as described herein, and detecting the binding of that compound to selected nicotinic receptor subtypes (e.g., α7 receptor subtype). Those skilled in the art of using diagnostic tools, such as PET and SPECT, can use the radiolabeled compounds described herein to diagnose a wide variety of conditions and disorders, including conditions and disorders associated with dysfunction of the central and autonomic nervous systems. Such disorders include a wide variety of CNS diseases and disorders, including Alzheimer's disease, Parkinson's disease, and schizophrenia. These and other representative diseases and disorders that can be evaluated include those that are set forth in U.S. Pat. No. 5,952,339 to Bencherif et al., the contents of which are hereby incorporated by reference.

In another aspect, the diagnostic compositions can be used in a method to monitor selective nAChR subtypes of a subject, such as a human patient. The method involves administering a detectably labeled compound as described herein to that patient and detecting the binding of that compound to selected nAChR subtypes (e.g., the α7 receptor subtype).

The following examples are provided to further illustrate the present invention, and should not be construed as limiting thereof.

IV. SYNTHETIC EXAMPLES

The following synthetic examples are provided to illustrate the present invention and should not be construed as limiting the scope thereof. In these examples, all parts and percentages are by weight, unless otherwise noted. Reaction yields are reported in mole percentage.

Compounds of the present invention are derivatives of 3-pyrid-3-yl-1,5-diazatricyclo[5.2.2.0<2,6>]undecane, the synthesis of which is described below:

2-((3-Pyridinyl)methylene)-1-azabicyclo[2.2.2]octan-3-one

Potassium hydroxide (56 g, 0.54 mole) was dissolved in methanol (420 mL). 3-Quinuclidinone hydrochloride (75 g, 0.49 mole) was added and the mixture was stirred for 30 min at ambient temperature. 3-Pyridinecarboxaldehyde (58 g, 0.54 mole) was added and the mixture stirred for 16 h at ambient temperature. The reaction mixture became yellow during this period, with solids caking on the walls of the flask. The solids were scraped from the walls and the chunks broken up. With rapid stirring, water (390 mL) was added. When the solids dissolved, the mixture was cooled at 4° C. overnight. The crystals were collected by filtration, washed with water, and air dried to obtain 80 g of yellow solid. A second crop (8 g) was obtained by concentration of the filtrate to ~10% of its former volume and cooling at 4° C. overnight. Both crops were sufficiently pure for further transformation (88 g, 82%).

2-(1-(3-Pyridinyl)-2-nitroethyl)-1-azabicyclo[2.2.2]octan-3-one 2-((3-Pyridinyl)methylene)-1-azabicyclo[2.2.2]octan-3-one (6.4 g, 0.024 mol) in dry methanol (45 mL) was added drop-wise to sodium methoxide (produced in situ, 0.036 mol). Nitromethane (3.7 mL, 0.068 mol) was then added, and the mixture was heated at reflux for 3 h. After cooling to room temperature, 1 N HCl was slowly added to adjust pH to 8. The mixture was concentrated by rotary evaporation to yield a solid brown residue. The residue was purified by column chromatography, using ethyl acetate/hexane (1:1, v/v), followed by chloroform/methanol/ammonia (90:10:1, v/v), as eluent, to obtain a yellow oil (4.2 g, 64%).

3-Pyridin-3-yl-1,5-diazatricyclo[5.2.2.0<2,6>]undecane 6-(1-(3-Pyridinyl)-2-nitroethyl)-1-azabicyclo[2.2.2]octan-3-one (14.0 g, 0.046 mol) was dissolved in ethanol (200 mL), and then Raney nickel was added under nitrogen. The mixture was subjected to hydrogenolysis (40 psi $H_2$) for 48 h and then filtered through Celite and concentrated by rotary evaporation to a crude brown residue. The residue was purified by column chromatography, using chloroform/methanol/ammonia (80:20:1, v/v) as eluent, to yield 3-pyridin-3-yl-1,5-diazatricyclo[5.2.2.0<2,6>]undecane as a yellow oil (8.0 g, 67%).

The following example describes the synthesis of various amide derivatives of 3-(3-pyridinyl)-1,5-diazatricyclo[5.2.2.0<2,6>]undecane.

Example 1

Amide derivatives of 3-pyridin-3-yl-1,5-diazatricyclo[5.2.2.0<2,6>]undecane

Benzotriazol-1-yloxytris(dimethylamino)phosphonium hexafluorophosphate (BOP, 0.097 g, 0.22 mmol) was added to a solution of the carboxylic acid (0.22 mmol) and triethylamine (0.66 mmol) in dichloromethane (1 mL), and then 3-pyridin-3-yl-1,5-diazatricyclo[5.2.2.0<2,6>]undecane (0.046 g, 0.20 mmol) was added. The mixture was stirred for 48 h at room temperature, then treated with 10% NaOH (0.2 mL). The biphasic mixture was separated by phase filtration, and the organic phase was concentrated on the Genevac centrifugal evaporator. The crude residue was dissolved in methanol (1 mL) and purified by HPLC on a C18 silica gel column, using acetonitrile/water gradient containing 0.05% trifluoroacetic acid.

Compounds made by this procedure were isolated as trifluoroacetate salts and characterized by LC/MS. Compounds exhibiting appropriate molecular ions and fragmentation patterns, and purities of 90% or greater were submitted for biological assessment. Selected compounds were analyzed by NMR spectroscopy, which confirmed their structural assignments. Table 1 lists molecular weights, calculated and measured by LC/MS, for some representative compounds, all of which bind at the α7 nAChR subtype with Ki values of <100 nM.

TABLE 1

| Compound # | Compound Name | Calc. FB Mass | LCMS Mass (MH+) |
|---|---|---|---|
| 1 | 5-(Benzofuran-2-ylcarbonyl)-3-pyridin-3-yl-1,5-diazatricyclo[5.2.2.0<2,6>]undecane | 373.459 | 374.32 |
| 2 | 5-(7-Methoxybenzofuran-2-ylcarbonyl)-3-pyridin-3-yl-1,5-diazatricyclo[5.2.2.0<2,6>]undecane | 403.485 | 404.35 |
| 3 | 5-(Naphth-2-ylcarbonyl)-3-pyridin-3-yl-1,5-diazatricyclo[5.2.2.0<2,6>]undecane | 383.498 | 384.35 |
| 4 | 5-(1H-Indol-3-ylcarbonyl)-3-pyridin-3-yl-1,5-diazatricyclo[5.2.2.0<2,6>]undecane | 372.474 | 373.38 |

The following example describes the synthesis of various urea derivatives of 3-(3-pyridinyl)-1,5-diazatricyclo[5.2.2.0<2,6>]undecane.

Example 2

Urea Derivatives of 3-pyridin-3-yl-1,5-diazatricyclo[5.2.2.0<2,6>]undecane

A mixture of 3-pyridin-3-yl-1,5-diazatricyclo[5.2.20<2,6>]undecane (0.20 mmol) and the appropriate isocyanate (0.22 mmol) were stirred in dry dichloromethane (1 mL) for 48 h at ambient temperature. Then the mixture was concentrated under reduced pressure and the residue was dissolved in methanol (0.75 mL) and purified by HPLC on a C18 silica gel column, using acetonitrile/water gradients containing 0.05% trifluoroacetic acid.

Compounds made by this procedure were isolated as trifluoroacetate salts and characterized by LC/MS. Compounds exhibiting appropriate molecular ions and fragmentation patterns, and purities of 90% or greater were submitted for biological assessment. Selected compounds were analyzed by NMR spectroscopy, which confirmed their structural assignments. Table 2 lists molecular weights, calculated and measured by LC/MS, for some representative compounds, all of which bind at the α7 nAChR subtype with Ki values of <100 nM.

TABLE 2

| Compound # | Compound Name | Calc. FB Mass | LCMS Mass (MH+) |
|---|---|---|---|
| 5 | 5-(N-(3,4-Dichlorophenyl)carbamoyl)-3-pyridin-3-yl-1,5-diazatricyclo[5.2.2.0<2,6>]undecane | 417.342 | 417.22 |
| 6 | 5-(N-(4-Bromophenyl)carbamoyl)-3-pyridin-3-yl-1,5-diazatricyclo[5.2.2.0<2,6>]undecane | 427.348 | ($^{81}$Br) |
| 7 | 5-(N-(4-Chlorophenyl)carbamoyl)-3-pyridin-3-yl-1,5-diazatricyclo[5.2.2.0<2,6>]undecane | 382.897 | 383.27 |
| 8 | 5-(N-(4-Methylthiophenyl)carbamoyl)-3-pyridin-3-yl-1,5-diazatricyclo[5.2.2.0<2,6>]undecane | 394.543 | 395.29 |

V. BIOLOGICAL ASSAYS

Example 3

Radioligand Binding at CNS nAChRs

α4β2 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The cerebral cortex was removed and placed in 20 volumes (weight: volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 μM, was added and the suspension was homogenized by Polytron. The homogenate was centrifuged at 18,000×g for 20 min at 4° C. and the resulting pellet was re-suspended in 20 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 4 mg protein/mL. Protein was determined by the method of Lowry et al., *J. Biol. Chem.* 193: 265 (1951), using bovine serum albumin as the standard.

The binding of [$^3$H]nicotine was measured using a modification of the methods of Romano et al., *Science* 210: 647 (1980) and Marks et al., *Mol. Pharmacol.* 30: 427 (1986). The [$^3$H]nicotine (Specific Activity=81.5 Ci/mmol) was obtained from NEN Research Products. The binding of [$^3$H]nicotine was measured using a 3 h incubation at 4° C. Incubations were conducted in 48-well micro-titre plates and contained about 400 μg of protein per well in a final incubation volume of 300 μL. The incubation buffer was PBS and the final concentration of [$^3$H]nicotine was 5 nM. The binding reaction was terminated by filtration of the protein containing bound ligand onto glass fiber filters (GF/B, Brandel) using a Brandel Tissue Harvester at 4° C. Filters were soaked in de-ionized water containing 0.33% polyethyleneimine to reduce non-specific binding. Each filter washed with ice-cold buffer (3×1 mL). Non-specific binding was determined by inclusion of 10 µM non-radioactive L-nicotine (Acros Organics) in selected wells.

The inhibition of [$^3$H]nicotine binding by test compounds was determined by including seven different concentrations of the test compound in selected wells. Each concentration was replicated in triplicate. $IC_{50}$ values were estimated as the concentration of compound that inhibited 50 percent of specific [$^3$H]nicotine binding. Inhibition constants (Ki values), reported in nM, were calculated from the $IC_{50}$ values using the method of Cheng et al., *Biochem. Pharmacol.* 22: 3099 (1973).

For initial screening, a single concentration of test compounds was tested in the above assay format with the following modifications. The binding of [$^3$H]epibatidine was measured. The [$^3$H]epibatidine (Specific Activity=48 Ci/mmol) was obtained from NEN Research Products. The binding of [$^3$H]epibatidine was measured using a 2 h incubation at 21° C. (room temperature). Incubations were conducted in 96-well Millipore Multiscreen (MAFB) plates containing about 200 µg of protein per well in a final incubation volume of 150 µL. The incubation buffer was PBS and the final concentration of [$^3$H]epibatidine was 0.3 nM. The binding reaction was terminated by filtration of the protein containing bound ligand onto the glass fiber filter base of the Multiscreen plates. Filters were soaked in de-ionized water containing 0.33% polyethyleneimine to reduce non-specific binding. Each filter was washed with ice-cold buffer (3×0.25 mL). Non-specific binding was determined by inclusion of 10 µM non-radioactive L-nicotine (Acros Organics) in selected wells. The single concentration of test compound was 5 µM and testing was performed in triplicate. 'Active' compounds were defined as compounds that inhibited the binding of [$^3$H]epibatidine to the receptor by at least 50% compared with the binding of [$^3$H]epibatidine in the absence of competitor. For those compounds found to be active in the single point screen, the inhibition constants (Ki values) were determined as described in the previous paragraphs of this section.

α7 nAChR Subtype

Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. Brains were removed and placed on an ice-cold platform. The hippocampus was removed and placed in 10 volumes (weight: volume) of ice-cold preparative buffer (137 mM NaCl, 10.7 mM KCl, 5.8 mM $KH_2PO_4$, 8 mM $Na_2HPO_4$, 20 mM HEPES (free acid), 5 mM iodoacetamide, 1.6 mM EDTA, pH 7.4); PMSF, dissolved in methanol to a final concentration of 100 µM, was added and the tissue suspension was homogenized by Polytron. The homogenate was centrifuged at 18,000×g for 20 min at 4° C. and the resulting pellet was re-suspended in 10 volumes of ice-cold water. After 60 min incubation on ice, a new pellet was collected by centrifugation at 18,000×g for 20 min at 4° C. The final pellet was re-suspended in 10 volumes of buffer and stored at −20° C. On the day of the assay, tissue was thawed, centrifuged at 18,000×g for 20 min, and then re-suspended in ice-cold PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) to a final concentration of approximately 2 mg protein/mL. Protein was determined by the method of Lowry et al., *J. Biol. Chem.* 193: 265 (1951), using bovine serum albumin as the standard.

The binding of [$^3$H]MLA was measured using a modification of the methods of Davies et al., *Neuropharmacol.* 38: 679 (1999). [$^3$H]MLA (Specific Activity=25-35 Ci/mmol) was obtained from Tocris. The binding of [$^3$H]MLA was determined using a 2 h incubation at 21° C. Incubations were conducted in 48-well micro-titre plates and contained about 200 µg of protein per well in a final incubation volume of 300 µL. The incubation buffer was PBS and the final concentration of [$^3$H]MLA was 5 nM. The binding reaction was terminated by filtration of the protein containing bound ligand onto glass fiber filters (GF/B, Brandel) using a Brandel Tissue Harvester at room temperature. Filters were soaked in de-ionized water containing 0.33% polyethyleneimine to reduce non-specific binding. Each filter washed with PBS (3×1 mL) at room temperature. Non-specific binding was determined by inclusion of 50 µM non-radioactive MLA in selected wells.

The inhibition of [$^3$H]MLA binding by test compounds was determined by including seven different concentrations of the test compound in selected wells. Each concentration was replicated in triplicate. $IC_{50}$ values were estimated as the concentration of compound that inhibited 50 percent of specific [$^3$H]MLA binding. Inhibition constants (Ki values), reported in nM, were calculated from the $IC_{50}$ values using the method of Cheng et al., *Biochem. Pharmacol.* 22: 3099 (1973).

For initial screening, a single concentration of test compounds was tested in the above assay format with the following modifications. Incubations were conducted in 96-well plates in a final incubation volume of 150 µL. Once the binding reaction was terminated by filtration onto glass fiber filters, the filters were washed four times with approximately 250 µL of PBS at room temperature. Non-specific binding was determined by inclusion of 10 µM non-radioactive MLA in selected wells. The single concentration of test compound was 5 µM and testing was performed in triplicate. 'Active' compounds were defined as compounds that inhibited the binding of [$^3$H]MLA to the receptor by at least 50% compared with the binding of [$^3$H]MLA in the absence of competitor. For those compounds found to be active in the single point screen, the inhibition constants (Ki values) were determined as described in the previous paragraphs of this section.

Determination of Dopamine Release

Dopamine release was measured using striatal synaptosomes obtained from rat brain, according to the procedures set forth by Rapier et al., *J. Neurochem.* 54: 937 (1990). Rats (female, Sprague-Dawley), weighing 150-250 g, were maintained on a 12 h light/dark cycle and were allowed free access to water and food supplied by PMI Nutrition International, Inc. Animals were anesthetized with 70% $CO_2$, then decapitated. The brains were quickly removed and the striata dissected. Striatal tissue from each of 2 rats was pooled and homogenized in ice-cold 0.32 M sucrose (5 mL) containing 5 mM HEPES, pH 7.4, using a glass/glass homogenizer. The tissue was then centrifuged at 1,000×g for 10 min. The pellet was discarded and the supernatant was centrifuged at 12,000×g for 20 min. The resulting pellet was re-suspended in perfusion buffer containing monoamine oxidase inhibitors (128 mM NaCl, 1.2 mM $KH_2PO_4$, 2.4 mM KCl, 3.2 mM $CaCl_2$, 1.2 mM $MgSO_4$, 25 mM HEPES, 1 mM ascorbic acid, 0.02 mM pargyline HCl and 10 mM glucose, pH 7.4) and centrifuged for 15 min at 25,000×g. The final pellet was resuspended in perfusion buffer (1.4 mL) for immediate use.

The synaptosomal suspension was incubated for 10 min at 37° C. to restore metabolic activity. [$^3$H]Dopamine ([$^3$H]DA, specific activity=28.0 Ci/mmol, NEN Research Products) was added at a final concentration of 0.1 µM and the suspension was incubated at 37° C. for another 10 min. Aliquots of tissue (50 µL) and perfusion buffer (100 µL) were loaded into the suprafusion chambers of a Brandel Suprafusion System (series 2500, Gaithersburg, Md.). Perfusion buffer (room temperature) was pumped into the chambers at a rate of 3 mL/min for a wash period of 8 min. Test compound (10 µM) or nicotine (10 µM) was then applied in the perfusion stream for 40 sec. Fractions (12 sec each) were continuously collected from each chamber throughout the experiment to capture basal release and agonist-induced peak release and to re-establish the baseline after the agonist application. The perfusate was collected directly into scintillation vials, to which scintillation fluid was added. [$^3$H]DA released was quantified by scintillation counting. For each chamber, the integrated area of the peak was normalized to its baseline.

Release was expressed as a percentage of release obtained with an equal concentration of L-nicotine. Within each assay, each test compound was replicated using 2-3 chambers; replicates were averaged. When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 4

Selectivity vs. Peripheral nAChRs

Interaction at the Human Muscle nAChR Subtype

Activation of muscle-type nAChRs was established on the human clonal line TE671/RD, which is derived from an embryonal rhabdomyosarcoma (Stratton et al., Carcinogen 10: 899 (1989)). These cells express receptors that have pharmacological (Lukas, J. Pharmacol. Exp. Ther. 251: 175 (1989)), electrophysiological (Oswald et al., Neurosci. Lett. 96: 207 (1989)), and molecular biological profiles (Luther et al., J. Neurosci. 9: 1082 (1989)) similar to the muscle-type nAChR.

TE671/RD cells were maintained in proliferative growth phase according to routine protocols (Bencherif et al., Mol. Cell. Neurosci. 2: 52 (1991) and Bencherif et al., J. Pharmacol. Exp. Ther. 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}$Rb$^+$ efflux according to the method described by Lukas et al., Anal. Biochem. 175: 212 (1988). On the day of the experiment, growth media was gently removed from the well and growth media containing $^{86}$Rubidium chloride (10$^6$ µCi/mL) was added to each well. Cells were incubated at 37° C. for a minimum of 3 h. After the loading period, excess $^{86}$Rb$^+$ was removed and the cells were washed twice with label-free Dulbecco's phosphate buffered saline (138 mM NaCl, 2.67 mM KCl, 1.47 mM KH$_2$PO$_4$, 8.1 mM Na$_2$HPO$_4$, 0.9 mM CaCl$_2$, 0.5 mM MgCl$_2$, Invitrogen/Gibco, pH. 7.4), taking care not to disturb the cells. Next, cells were exposed to either 100 µM of test compound, 100 µM of L-nicotine (Acros Organics) or buffer alone for 4 min. Following the exposure period, the supernatant containing the released $^{86}$Rb$^+$ was removed and transferred to scintillation vials. Scintillation fluid was added and released radioactivity was measured by liquid scintillation counting.

Within each assay, each point had 2 replicates, which were averaged. The amount of $^{86}$Rb$^+$ release was compared to both a positive control (100 µM L-nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Rat Ganglionic nAChR Subtype

Activation of rat ganglion nAChRs was established on the pheochromocytoma clonal line PC12, which is a continuous clonal cell line of neural crest origin, derived from a tumor of the rat adrenal medulla. These cells express ganglion-like nAChRs (see Whiting et al., Nature 327: 515 (1987); Lukas, J. Pharmacol. Exp. Ther. 251: 175 (1989); Whiting et al., Mol. Brain. Res. 10: 61 (1990)).

Rat PC12 cells were maintained in proliferative growth phase according to routine protocols (Bencherif et al., Mol. Cell. Neurosci. 2: 52 (1991) and Bencherif et al., J. Pharmacol. Exp. Ther. 257: 946 (1991)). Cells were cultured in Dulbecco's modified Eagle's medium (Gibco/BRL) with 10% horse serum (Gibco/BRL), 5% fetal bovine serum (HyClone, Logan Utah), 1 mM sodium pyruvate, 4 mM L-Glutamine, and 50,000 units penicillin-streptomycin (Irvine Scientific). When cells were 80% confluent, they were plated to 6 well Nunc plates (Nunclon) and coated with 0.03% poly-L-lysine (Sigma, dissolved in 100 mM boric acid). Experiments were conducted when the cells reached 80% confluency.

Nicotinic acetylcholine receptor (nAChR) function was assayed using $^{86}$Rb$^+$ efflux according to a method described by Lukas et al., Anal. Biochem. 175: 212 (1988). On the day of the experiment, growth media was gently removed from the well and growth media containing $^{86}$Rubidium chloride (10$^6$ µCi/mL) was added to each well. Cells were incubated at 37° C. for a minimum of 3 h. After the loading period, excess $^{86}$Rb$^+$ was removed and the cells were washed twice with label-free Dulbecco's phosphate buffered saline (138 mM NaCl, 2.67 mM KCl, 1.47 mM KH$_2$PO$_4$, 8.1 mM Na$_2$HPO$_4$, 0.9 mM CaCl$_2$, 0.5 mM MgCl$_2$, Invitrogen/Gibco, pH. 7.4), taking care not to disturb the cells. Next, cells were exposed to either 100 µM of test compound, 100 µM of nicotine or buffer alone for 4 min. Following the exposure period, the supernatant containing the released $^{86}$Rb$^+$ was removed and transferred to scintillation vials. Scintillation fluid was added and released radioactivity was measured by liquid scintillation counting.

Within each assay, each point had 2 replicates, which were averaged. The amount of $^{86}$Rb$^+$ release was compared to both a positive control (100 µM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also determined.

Interaction at the Human Ganglionic nAChR Subtype

The cell line SH-SY5Y is a continuous line derived by sequential subcloning of the parental cell line, SK-N-SH, which was originally obtained from a human peripheral neuroblastoma. SH-SY5Y cells express a ganglion-like nAChR (Lukas et al., *Mol. Cell. Neurosci.* 4: 1 (1993)).

Human SH-SY5Y cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). Cells were cultured in Dulbecco's modified Eagle's medium (Gibco/BRL) with 10% horse serum (Gibco/BRL), 5% fetal bovine serum (Hy-Clone, Logan Utah), 1 mM sodium pyruvate, 4 mM L-Glutamine, and 50,000 units penicillin-streptomycin (Irvine Scientific). When cells were 80% confluent, they were plated to 6 well polystyrene plates (Costar). Experiments were conducted when the cells reached 100% confluency.

Nicotinic acetylcholine receptor (nAChR) function was assayed using $^{86}Rb^+$ efflux according to a method described by Lukas et al., *Anal. Biochem.* 175: 212 (1988). On the day of the experiment, growth media was gently removed from the well and growth media containing $^{86}$Rubidium chloride ($10^6$ μCi/mL) was added to each well. Cells were incubated at 37° C. for a minimum of 3 h. After the loading period, excess $^{86}Rb^+$ was removed and the cells were washed twice with label-free Dulbecco's phosphate buffered saline (138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4), taking care not to disturb the cells. Next, cells were exposed to either 100 μM of test compound, 100 μM of nicotine, or buffer alone for 4 min. Following the exposure period, the supernatant containing the released $^{86}Rb^+$ was removed and transferred to scintillation vials. Scintillation fluid was added and released radioactivity was measured by liquid scintillation counting.

Within each assay, each point had 2 replicates, which were averaged. The amount of $^{86}Rb^+$ release was compared to both a positive control (100 μM nicotine) and a negative control (buffer alone) to determine the percent release relative to that of L-nicotine.

When appropriate, dose-response curves of test compound were determined. The maximal activation for individual compounds (Emax) was determined as a percentage of the maximal activation induced by L-nicotine. The compound concentration resulting in half maximal activation ($EC_{50}$) of specific ion flux was also defined.

Example 5

Determination of Binding at Non-Nicotinic Receptors

Muscarinic M3 Subtype

The human clonal line TE671/RD, derived from an embryonal rhabdomyosarcoma (Stratton et al., *Carcinogen* 10: 899 (1989)), was used to define binding to the muscarinic M3 receptor subtype. As evidenced through pharmacological (Bencherif et al., *J. Pharmacol. Exp. Ther.* 257: 946 (1991) and Lukas, *J. Pharmacol. Exp. Ther.* 251: 175 (1989)), electrophysiological (Oswald et al., *Neurosci. Lett.* 96: 207 (1989)), and molecular biological studies (Luther et al., *J. Neurosci.* 9: 1082 (1989)) these cells express muscle-like nicotinic receptors.

TE671/RD cells were maintained in proliferative growth phase according to routine protocols (Bencherif et al., *Mol. Cell. Neurosci.* 2: 52 (1991) and Bencherif et al., *J. Pharmacol. Exp. Ther.* 257: 946 (1991)). They were grown to confluency on 20-150 mm tissue culture treated plates. The media was then removed and cells scraped using 80 mL of PBS (Dulbecco's Phosphate Buffered Saline, 138 mM NaCl, 2.67 mM KCl, 1.47 mM $KH_2PO_4$, 8.1 mM $Na_2HPO_4$, 0.9 mM $CaCl_2$, 0.5 mM $MgCl_2$, Invitrogen/Gibco, pH 7.4) and then centrifuged at 1000 rpm for 10 min. The supernatant was then suctioned off and the pellet(s) stored at −20° C. until use.

On the day of the assay, the pellets were thawed, re-suspended with PBS and centrifuged at 18,000×g for 20 min, then re-suspended in PBS to a final concentration of approximately 4 mg protein/mL and homogenized by Polytron. Protein was determined by the method of Lowry et al., *J. Biol. Chem.* 193: 265 (1951), using bovine serum albumin as the standard.

The binding of [$^3$H]QNB was measured using a modification of the methods of Bencherif et al., *J. Pharmacol. Exp. Ther.* 257: 946 (1991). [$^3$H]QNB (Specific Activity=30-60 Ci/mmol) was obtained from NEN Research Products. The binding of [$^3$H]QNB was measured using a 3 h incubation at 4° C. Incubations were conducted in 48-well micro-titre plates and contained about 400 μg of protein per well in a final incubation volume of 300 μL. The incubation buffer was PBS and the final concentration of [$^3$H]QNB was 1 nM. The binding reaction was terminated by filtration of the protein containing bound ligand onto glass fiber filters (GF/B, Brandel) using a Brandel Tissue Harvester at 4° C. Filters were pre-soaked in de-ionized water containing 0.33% polyethyleneimine to reduce non-specific binding. Each filter washed with ice-cold buffer (3×1 mL). Non-specific binding was determined by inclusion of 10 μM non-radioactive atropine in selected wells.

The inhibition of [$^3$H]QNB binding by test compounds was determined by including seven different concentrations of the test compound in selected wells. Each concentration was replicated in triplicate. $IC_{50}$ values were estimated as the concentration of compound that inhibited 50 percent of specific [$^3$H]QNB binding. Inhibition constants (Ki values), reported in mM, were calculated from the $IC_{50}$ values using the method of Cheng et al., *Biochem. Pharmacol.* 22: 3099 (1973).

Example 6

Determination of Activity at the α7 nAChR Subtype

Selective α7 agonists can be found using a functional assay on FLIPR (see, for example, PCT WO 00/73431 A2, the contents of which are hereby incorporated by reference), which is a commercially available high throughput assay (Molecular Devices Corporation, Sunnyvale, Calif.). FLIPR is designed to read the fluorescent signal from each well of a 96 or 384 well plate as fast as twice a second for up to 30 minutes. This assay can be used to accurately measure the functional pharmacology of α7 nAChR and $5HT_3R$ subtypes. Cell lines that express functional forms of the α7 nAChR subtype, using the α7/5-$HT_3$ channel as the drug target and/or cell lines that express functional 5-$HT_3$, are used to conduct the assay. In both cases, the ligand-gated ion channels are expressed in SH-EP1 cells. Both ion channels can produce a robust signal in the FLIPR assay. Using the FLIPR assay, the compounds described herein can be evaluated for their ability to function as agonists, partial agonists or antagonists at the α7 nAChR subtype.

Example 7

Summary of Biological Activity

Compounds of the present invention exhibit Ki values at the α7 subtype in the nM-□M range, indicating that they have very high affinity for the α7 nAChR subtype. High-throughput screening indicated that none of the compounds bound to α4β2 nAChR subtypes with any significant affinity (Ki values>10 μM).

Compounds of the present invention exhibited little or no agonist activity in functional models bearing muscle-type receptors (α1β1γδ subtype in human TE671/RD clonal cells), or ganglion-type receptors α3β4 subtype in the Shooter subclone of rat pheochromocytoma PC12 cells and in human SHSY-5Y clonal cells), generating only 1-12% (human muscle), 1-19% (rat ganglion) and 1-15% (human ganglion) of nicotine's response at these subtypes. These data indicate selectivity for CNS over PNS nAChRs. Because similar compounds had been described by others as exhibiting muscarinic activity (see, for instance, U.S. Pat. No. 5,712,270 to Sabb and PCTs WO 02/00652 and WO 02/051841), representative compounds (#s 1, 2, 4, 9 and 11) were evaluated for their ability to inhibit [³H]QNB binding at muscarinic sites in the human clonal line TE671/RD. None of the compounds was able to inhibit [³H]QNB binding, indicating that these compounds do not bind to human M3 receptors. Thus, compounds of the present invention are distinguished in their in vitro pharmacology from reference compounds (see, for instance, U.S. Pat. No. 5,712,270 to Sabb and PCTs WO 02/00652 and WO 02/051841) by virtue of the inclusion, in their structure, of the 3-pyridinylmethyl substitutent in the 2 position of the 1-azabicycle.

The data show that the compounds of the present invention are potent α7 nicotinic ligands that selectively bind at α7 nAChR subtypes. In contrast, the compounds of the present invention do not bind well at those subtypes of the nAChR that are characteristic of the peripheral nervous system or at M3 muscarinic receptors. Thus, the compounds of the present invention possess therapeutic potential in treating central nervous system disorders without producing side effects associated with interaction with the peripheral nervous system. The affinity of these ligands for α7 nAChR subtypes is tolerant of a wide variety of aryl (Ar in Formula 1) groups and substitutents thereon. Furthermore, the synthesis is straightforward, efficient and amenable to massively parallel protocols.

Having disclosed the subject matter of the present invention, it should be apparent that many modifications, substitutions and variations of the present invention are possible in light thereof. It is to be understood that the present invention can be practiced other than as specifically described. Such modifications, substitutions and variations are intended to be within the scope of the present application.

That which is claimed is:

1. A compound having a structure of the formula:

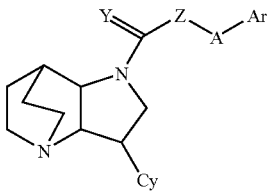

wherein:
Y is either oxygen or sulfur,
Z is either NH or a covalent bond,
A is either absent or a linker species selected from the group —CR'R"—, —CR'R"—CR'R"—, —CR'═CR'—, and —C$_2$—, wherein R' and R" are as hereinafter defined,
Ar is indole, benzofuran, or benzothiophene; and
Cy is pyridine,
wherein, Ar can be unsubstituted or can be substituted with 3 one or more substituents selected from the group consisting of alkyl, alkenyl, cycloalkyl, aryl, substituted aryl, arylalkyl, substituted arylalkyl, halo —OR', —NR'R", —CF$_3$, —CN, —NO$_2$, —C$_2$R', —SR', —N$_3$, —C(═O)NR'R", —NR'C(═O)R", —C(═O)R', —C(═O)OR', —OC(═O)R', —O(CR'R")$_r$C(═O)R', O(CR'R")$_r$NR"C(═O)R', —O(CR'R")$_r$NR"SO2R', —OC(═O)NR'R", —NR'C(═O)O—R", SO$_2$R', —SO$_2$NR'R", and —NR'SO$_2$R", where R' and R" are individually hydrogen, alkyl C$_1$-C$_8$ alkyl, cycloalkyl, aryl, or arylalkyl, and r is an integer from 1 to 6,
or a radiolabeled version thereof
or a pharmaceutically acceptable salt thereof.

2. The compound of claim 1, wherein Y is O, and Z is NH.

3. The compound of claim 1, wherein Y is O and Z is a covalent bond.

4. The compound selected from the group consisting of:
5-(benzothien-2-ylcarbonyl)-3-pyridin-3-yl-1,5-diazatricyclo[5.2.2.0<2,6>]undecane,
5-(benzofuran-2-ylcarbonyl)-3-pyridin-3-yl-1,5-diazatricyclo[5.2.2.0<2,6>]undecane,
5-(7-methoxybenzofuran-2-ylcarbonyl)-3-pyridin-3-yl-1,5-diazatricyclo[5.2.2.0<2,6>]undecane, and
5-(1H-indol-3-ylcarbonyl)-3-pyridin-3-yl-1,5-diazatricyclo[5.2.2.0<2,6>]undecane.

5. The compound of claim 1, wherein A is absent.

6. A pharmaceutical composition comprising a pharmaceutical carrier and a compound of claim 1.

7. The compound or composition of claim 1, wherein the compound is radiolabeled.

8. The compound of composition of claim 1, wherein the compound comprises $^{11}$C, $^{18}$F, $^{76}$Br, $^{123}$I or $^{125}$I.

* * * * *